United States Patent
Sandler et al.

(10) Patent No.: US 10,113,149 B2
(45) Date of Patent: Oct. 30, 2018

(54) REPROGRAMMING OF HUMAN ENDOTHELIUM INTO HEMATOPOIETIC MULTI-LINEAGE PROGENITORS BY DEFINED FACTORS

(71) Applicant: CORNELL UNIVERSITY, Ithaca, NY (US)

(72) Inventors: Vladislav M. Sandler, New York, NY (US); Shahin Rafii, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/760,773

(22) PCT Filed: Jan. 15, 2014

(86) PCT No.: PCT/US2014/011575
§ 371 (c)(1),
(2) Date: Jul. 14, 2015

(87) PCT Pub. No.: WO2014/113415
PCT Pub. Date: Jul. 24, 2014

(65) Prior Publication Data
US 2015/0361398 A1    Dec. 17, 2015

Related U.S. Application Data

(60) Provisional application No. 61/752,688, filed on Jan. 15, 2013.

(51) Int. Cl.
| | |
|---|---|
| *C12N 15/85* | (2006.01) |
| *C12N 5/0789* | (2010.01) |
| *A61K 35/28* | (2015.01) |
| *A61K 35/44* | (2015.01) |
| *A61K 35/12* | (2015.01) |

(52) U.S. Cl.
CPC ............ *C12N 5/0647* (2013.01); *A61K 35/28* (2013.01); *A61K 35/44* (2013.01); *A61K 2035/124* (2013.01); *C12N 2500/90* (2013.01); *C12N 2501/11* (2013.01); *C12N 2501/115* (2013.01); *C12N 2501/125* (2013.01); *C12N 2501/145* (2013.01); *C12N 2501/2303* (2013.01); *C12N 2501/2306* (2013.01); *C12N 2501/26* (2013.01); *C12N 2501/60* (2013.01); *C12N 2506/28* (2013.01)

(58) Field of Classification Search
None
See application file for complete search history.

(56) References Cited

U.S. PATENT DOCUMENTS

2008/0241171 A1    10/2008    Gentry et al.
2012/0129262 A1    5/2012     West et al.

FOREIGN PATENT DOCUMENTS

| JP | 2010220581 A | 10/2010 |
|---|---|---|
| RU | 2359030 C1 | 6/2009 |
| WO | 2005100549 A1 | 10/2005 |
| WO | 2012109208 A2 | 8/2012 |

OTHER PUBLICATIONS

Broxmeyer et al. PNAS, 1989. vol. 86, pp. 3828-3832.*
Chotinantakul, K. et al., "Hematopoietic Stem Cell Development, Niches, and Signaling Pathways", Bone Marrow Research, (Jan. 1, 2012), vol. 18, No. 55, 15 pages.
Wisniewski, D. et al., "Further phenotypic characterization of the primitive lineage—CD34 + CD38− CD90 + CD45RA− hematopoietic stem cell/progenitor cell sub-population islated from cord blood, moblized peripheral blood and piatents with chronic myelogenous leukemia", Blood Cancer Journal, (Sep. 1, 2011), vol. 1, No. 9, 11 pages.
Szabo, E. et al., "Direct conversion of human fibroblasts to multilineage blood progenitors", Nature, (Nov. 25, 2010), vol. 468, No. 7323, pp. 521-528.
Chen, M.J. et al., "Runx1 is required for the endothelial to haematopoietic cell transition but not thereafter", Nature, (Feb. 12, 2009), vol. 457, No. 7231, pp. 887-891.
European Search Report dated May 5, 2016 issued in EP 14 74 0745.6.
European Communication dated Aug. 21, 2015 received from Application No. 14740745.6.
Chinese Office Action dated Aug. 7, 2017 issued in corresponding Chinese Patent Application No. 201480015604.1.
Japanese Office Action dated Dec. 12, 2017 issued in JP Patent Application No. 2015-552909, with English translation.
Butler, J.M., et al. "Development of a vascular niche platform for expansion of repopulating human cord blood stem and progenitor cells." Blood, 2012, vol. 120, No. 6, pp. 1344-1347.
Russian Office Action dated Jan. 17, 2018 issued in corresponding Russian Patent Application No. 2015134394.
Chotinantakul K. et al., "Hematopoietic Stem Cell Development, Niches, and Signaling Pathways", Bone Marrow Research, 2012, vol. 2012, 16 pages, doi:10.1155/2012/270425.
Wisniewski D. et al.,"Further phenotypic characterization of the primitive lineage—CD34+CD38−CD90+CD45RA hematopoietic stem cell/progenitor cell sub-population isolated from cord blood, mobilized peripheral blood and patients with chronic myelogenous leukemia" Blood Cancer Journal, 2011, vol. 1, 11 pages, doi:10.1038/bcj.2011.35.
Amit, M. et al. "Clonally derived human embryonic stem cell lines maintain pluripotency and proliferative potential for prolonged periods of culture", Developmental Biology, 2000, vol. 227, pp. 271-278, doi:10.1006/dbio.2000.9912.

* cited by examiner

*Primary Examiner* — Celine Qian
(74) *Attorney, Agent, or Firm* — Scully Scott Murphy & Presser

(57) ABSTRACT

The invention is directed to generation of hematopoietic multi-lineage progenitors (HMLPs) from endothelial cells (ECs) by effecting forced expression of certain transcription factors in the ECs and culturing the ECs in serum free media in the presence of endothelial feeder cells. The HMLPs generated in accordance with this invention can produce erythroid, lymphoid, myeloid, and megakaryocyte cells. These generated HMLPs can be used in therapeutic treatment of disorders including hematopoietic conditions.

19 Claims, 28 Drawing Sheets

REPROGRAMMING OF HUMAN ENDOTHELIUM INTO HEMATOPOIETIC MULTI-LINEAGE PROGENITORS BY DEFINED FACTORS

CROSS-REFERENCE TO RELATED APPLICATIONS

This application claims priority to U.S. provisional application 61/752,688, filed Jan. 15, 2013, which is incorporated herein in its entirety.

STATEMENT REGARDING FEDERALLY SPONSORED RESEARCH OR DEVELOPMENT

This invention was made with government support under Grant No. HL097797, awarded by the National Institutes of Health. The government has certain rights in the invention.

BACKGROUND OF THE DISCLOSURE

Somatic cells have been reprogrammed into the pluripotent state by nuclear transfer (Gurdon, J. B. et al., *Nature* 182:64-65 (1958); Eggan, K. et al., *Nature*) 428:44-49 (2004), Noggle, S. et al, *Nature* 478:70-75 (2011)), cell fusion (Tada, M. et al., *Curr Biol* 11:1553-1558 (2001); Cowan, C. A. et al., *Science* 309:1369-1373 (2005); Blau, H. M. et al., *Semin Cell Dev Biol* 10:267-272 (1999)), and forced expression of transcription factors (Takahashi, K. et al., *Cell* 131:861-872 (2007); Chen, M. J. et al., *Cell Stem Cell* 9:541-552 (2011)). Somatic cells have also been reprogrammed into terminally differentiated cells such as myoblasts (Davis, R. L. et al, *Cell* 51:987-1000 (1987)), macrophage-like cells (Xie, H. et al., *Cell* 117:663-676 (2004)), beta-cells (Zhou, Q. et al., *Nature* 455:627-632 (2008)), hepatocyte-like cells (Sekiya, S. et al., *Nature* 475:390-393 (2011)), neurons (Vierbuchen, T. et al., *Nature* 463:1035-1041 (2010)) and endothelial cells (Ginsberg, M. et al., *Cell* 151:559-575 (2012)). A number of groups recently reported direct reprogramming of fibroblasts into neural stem cells/multi-lineage neural progenitors (Han, D. W. et al., *Cell Stem Cell* 10:465-472 (2012); Lujan, E. et al., *Proc Natl Acad Sci USA* 109:2527-2532 (2012); Thier, M. et al., *Cell Stem Cell* 10:473-479 (2012)). However, direct conversion of the somatic cells into functional engraftable multi-lineage hematopoietic stem and progenitor cells (HSPCs) has been difficult to achieve (Szabo, E. et al. *Nature* 468:521-526 (2010); Chambers, S. M. et al., *Cell* 145:827-830 (2011); Pereira, C. F. et al., *Cell Stem Cell* 13:205-218 (2013)).

During murine development, definitive hematopoietic stem cells (HSCs) originate in the dorsal aorta within the aorta-gonad-mesonephros (AGM) region (North, T. E. et al., *Immunity* 16:661-672 (2002); de Bruijn, M. F. et al., *EMBO J* 192:465-2474 (2000); Medvinsky, A. et al., *Cell* 86:897-906 (1996)). In vertebrates, including zebra fish, murine, and possibly human, HSCs are believed to emerge from the layer of hemogenic vascular cells lining the dorsal aorta floor and umbilical arteries (Zovein, A. C. et al., *Cell Stem Cell* 3:625-636 (2008); Boisset, J. C. et al., *Nature* 464:116-120 (2010); Bertrand, J. Y. et al., *Nature* 464:108-111 (2010); Kissa, K. et al., *Nature* 464:112-115 (2010)). This process depends on the expression of transcription factor (TF) RUNX1 (Chen, M. J. et al., *Nature* 457:887-891 (2009)). Close association of developing endothelial cells (ECs) and HSPCs in the conceptus has led to an EC-hematopoietic transition theory of hematopoiesis (Zovein, A. C. et al., *Cell Stem Cell* 3:625-636 (2008)).

Although it is known that HSCs and definitive erythroid/myeloid progenitors (EMPs) arise from multiple sites containing hemogenic ECs, it has been difficult to characterize the molecular programs driving the spontaneous ontogenetic transition of primitive hemogenic ECs to hematopoietic progenitors (Chen, M. J. et al., *Nature* 457:887-891 (2009); North, T. E. et al., *Cell* 137:736-748 (2009)) because the identity of key molecules and the sequence of their activity remains elusive (Orkin, S. H. et al., *Cell* 132:631-644 (2008)). Differential expression of TFs in hemogenic ECs progeny is linked to the early developmental decision to yield definitive HSPCs or ECs (Chen, M. J. et al. *Cell Stem Cell* 9:541-552 (2011)) However, it is not clear whether TFs direct these cellular fate decisions or simply promote pre-determined programs in the hemogenic ECs. Microenvironmental cues provided by anatomically distinct niches—such as those within the AGM, fetal liver and placenta—are also required for physiologic expansion of primitive HSCs and effective hematopoietic development (Gekas, C. et al., *Dev Cell* 8:365-375 (2005)).

Modern methods of treatment of blood disorders rely on transplantation of healthy HSPCs. Currently, there are two major methods of producing a sufficient number of allogeneic and autologous HSPCs, both of which have limitations: (1) ex-vivo expansion of HSPCs (e.g. HSPCs from cord blood); and (2) directed differentiation of pluripotent cells into HSPCs. Ex-vivo expansion of healthy HSPCs is limited by donor availability and complicated by purification methods in the case of autologous transplant and HLA matching in the case of allogeneic transplantation. Directed differentiation of pluripotent cells is limited by our understanding of hematopoietic system development as well as generation of stable ECs, and is yet to yield sufficient quantities of adult transplantable HSPCs.

BRIEF SUMMARY OF THE DISCLOSURE

The invention is directed to generation of hematopoietic multi-lineage progenitors (HMLPs) from endothelial cells (ECs) by effecting forced expression of certain transcription factors in the ECs and culturing the ECs in serum free media in the presence of endothelial feeder cells. The HMLPs generated in accordance with this invention can produce erythroid, lymphoid, myeloid, and megakaryocyte cells. These generated HMLPs are capable of engrafting in mice, and therefore can be used in therapeutic treatment of disorders including hematopoietic conditions.

Accordingly, this disclosure provides methods of generating human hematopoietic multi-lineage progenitor cells (HMLPs) from human endothelial cells (ECs). The methods involve culturing ECs that are transformed to express each of the transcription factors Finkel-Biskis-Jinkins murine osteosarcoma viral oncogene homolog B (FOSB), growth factor independent 1 transcription repressor (GFI1), Runt-related transcription factor 1 (RUNX1), spleen focus forming virus proviral integration oncogene (SPI1), or functional homologs or derivatives of FOSB, GFI1, RUNX1, and SPI1, in serum-free media with endothelial feeder cells.

ECs that can be used to generate HMLPs include fetal, neonatal, adult, and progenitor ECs. In some embodiments, the ECs are selected from human umbilical vascular endothelial cells (HUVECs) or adult dermal micro-vascular endothelial cells (hDMECs).

In some embodiments, forced expression of transcription factors is effected by transduction of ECs with one or more vectors driving expression of FOSB, GFI1, RUNX1, and SPI1. At least one of these vectors can also include a selectable marker, such as an antibiotic resistance marker, an enzymatic marker, an epitope marker, or a visual marker. Prior to culturing in the presence of the endothelial feeder cells, the ECs can be enriched for expression of FOSB, GFI1, RUNX1, and/or SPI1 by selecting cells expressing at least one selectable marker. In some embodiments, the expression of one or more of FOSB, GFI1, RUNX1, and SPI1 is inducible and/or transient.

Endothelial feeder cells can be selected from a variety of ECs. In some embodiments, the feeder cells are human umbilical vascular endothelial cells (HUVECs) transformed to express a gene selected from: the adenovirus E4 open reading frame 1 (E4ORF1) gene, or the Akt gene.

ECs can be grown in the presence of endothelial feeder cells in a serum-free hematopoietic medium, such as a serum-free hematopoietic stem cell medium. The serum-free hematopoietic medium can include growth factors and/or cytokines, particularly bFGF, EGF, SCF, FLT3, TPO, and IL-6. The serum-free hematopoietic medium can also include IGF-1, IGF-2, and IL-3. ECs can be cultured for at least five days to generate HMLPs. HMLPs can be isolated from the cell culture based on selection of $CD45^+$ cells. In some embodiments, HMLPs are selected by selection of $CD45^+CD34^+$ cells. HMLPs generated are typically a heterogenous mixture of cells, but in particular embodiments, a mixture of HMLPs include cells that are $CD45^+Lin^-CD45RA^-CD38^-CD90^+CD34^+$ and/or $CD45^+Lin^-CD45RA^-CD38^-CD90^+CD34^+$.

Further provided in this disclosure are populations of HMLPs produced according to the disclosed methods. A composition comprising HMLPs produced according to the method of claim 1 in a pharmaceutically acceptable carrier.

Also provided herein are methods of treating hematopoietic disorders, involving administering EC-generated HMLPs to a subject in need of treatment. HMLPs can differentiate into hematopoietic cells after transplantation into a recipient. The hematopoietic disorder can be selected from, for example, leukemia or lymphoma. The HMLPs administered to the subject can be autologous to the subject, or allogeneic to the subject. HMLPs generated according to the disclosed methods do not cause malignant transformation in a recipient.

DETAILED DESCRIPTION OF THE DISCLOSURE

Figure 1A:
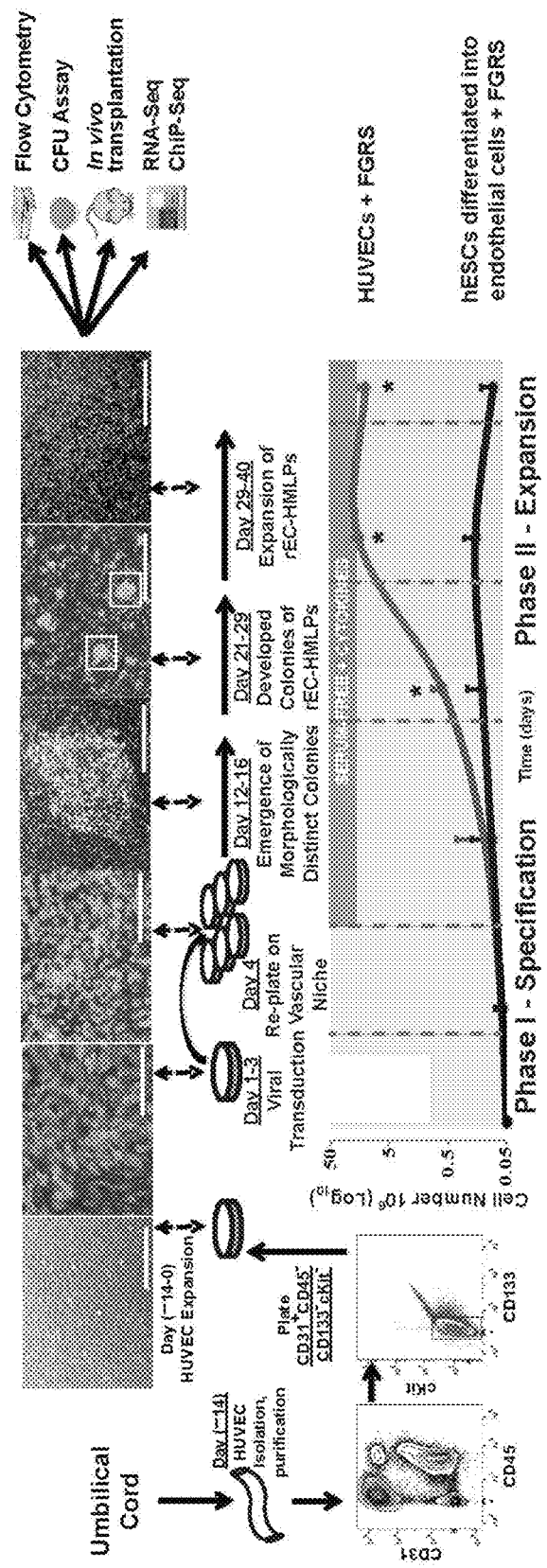
FIGS. 1A-1E. A. Schema of reprogramming platform of HUVECs into hematopoietic multi-lineage progenitors (rEC-HMLPs). HUVECs were isolated from discarded umbilical cord, sorted for a pure population of phenotypically marked $CD45^-CD133^-cKit^-CD31^+$ endothelial cells (ECs) and expanded for further experimentation (days −14 to 0). HUVECs were transduced with FGRS and allowed to stabilize expression of transgenes (days 1-3). Transduced HUVECs were plated at 1/6th density (day 4) and grown on a vascular niche-like layer of $E4ORF1^+$ HUVECs (E4-HUVECs) in serum-free media (days 12-40). Distinct flat colonies were observed about two weeks after seeding transduced cells on a vascular niche-like layer (days 12-16). Over time (days 21-29) some of these colonies gave rise to three-dimensional grape-like structures representing putative rEC-HMLPs. After a month (days 29-40) rEC-HMLPs expanded profusely giving rise to prototypical hematopoietic colonies. The process of reprogramming is subdivided into two phases: Phase I—Specification and Phase II—Expansion. The expanding cultures were routinely assayed for morphological change, cell number, and expression of the pan-hematopoietic marker CD45. Grey trace represents cell number dynamics in the reprogramming of HUVECs into rEC-HMLPs. Black line illustrates low expansion potential of differentiating hES-ECs cells into hematopoietic progenitors. B. Emergence of rounded hematopoietic-like $CD45^+$ cells two to three weeks after HUVECs were transduced with a set of TFs (white arrows). Scale bar is 200 µm. C. Generation of hematopoietic-like clusters from FGRS transduced HUVECs is enhanced by co-culturing with vascular niche and serum-free environment and blocked by the presence of serum. D. One-by-one elimination of TFs revealed a minimal set of factors (FOSB, GFI1, RUNX1, and SPI1) capable of generating hematopoietic-like colonies in the HUVEC culture. A set of 26 TFs minus one TF was evaluated for the ability to evoke formation of hematopoietic-like clusters (n=3). Asterisks show statistically significant ($p<0.05$) reduction of the number of hematopoietic-like clusters in the transduced HUVECs compared to the full set of TFs. Control represents non-transduced HUVECs. Transduced cells were cultured on a layer of non-transduced E4-HUVECs in serum-free hematopoietic media. E. One-by-one elimination of the FGRS factors shows that all four FGRS factors are necessary and sufficient for generation of long-lasting hematopoietic-like colonies.

Provided herein are methods to reprogram endothelial cells (ECs) into hematopoietic multi-lineage progenitors (HMLPs or rEC-HMLPs). The methods include culturing EC cells with a set of transcription factors (TFs)—including FOSB, GFI1, RUNX1, and SPI1 (FGRS)—that efficiently reprogram ECs such as human umbilical vein ECs (HUVECs) and human adult dermal microvascular ECs (hDMECs) into HMLPs.

Human hematopoietic multi-lineage progenitors (HMLPs), as referenced herein, are cells that have the ability or potential to generate, or differentiate into, multiple types of hematopoietic lineage cells. The hematopoietic lineages, and the differentiated cells encompassed by these lineages, are myeloid lineage cells, which include erythrocytes, monocytes, macrophages, megakaryocytes, myeloblasts, dendritic cells, and granulocytes (basophils, neutrophils, eosinophils, and mast cells); and lymphoid lineage cells, which include T lymphocytes/T cells, B lymphocytes/B cells, and natural killer cells. The HMLPs generated by the methods disclosed herein have the ability to generate hematopoietic cells of myeloid and lymphoid lineages, including T cells, B cells, erythrocytes, monocytes, macrophages, megakaryocytes, myeloblasts, dendritic cells, and granulocytes.

HMLPs as disclosed herein have the ability to engraft (establish residency) and provide long term repopulation of hematopoietic cells following transplantation into a recipient. The disclosed HMLPs maintain their multi-lineage potential after engraftment, and are also capable of subsequent engraftment from one recipient to one or more additional recipients, while still maintaining multi-lineage potential. Capacity for long term engraftment (e.g., for 4 weeks, 8 weeks, 12 weeks, 16 weeks, or 20 weeks or longer post-transplantation), maintenance of multi-lineage potential, and secondary engraftment, are each highly desirable in a cell population for application to treatment of hematopoietic disorders.

HMLPs can be defined by the expression of cell surface markers. Although HMLPs represent a heterogeneous population of cells, the cells are characterized in part by the expression of CD45 (i.e., the cells are $CD45^+$). In a particular embodiment, HMLPs are $CD45^+CD34^+$. HMLPs can further be $CD90^+$ and/or $CD38^+$.

HMLPs generated in accordance with this invention are non-homogenous and contain a mixture of cell types, with each cell type displaying distinct cell markers, distinct morphologies, and/or distinct levels of differentiation. In specific embodiments, HMLPs contain at least one progenitor cell capable of differentiating into a cell of myeloid and/or lymphoid lineage. In a particular embodiment, a population of HMLPs contains at least 0.01% to at least 0.4% of the total number of cells in the population, or at least 10 cells per million to at least 250 cells per million in the population, of progenitor cells expressing the markers $CD45^+Lin^-CD45RA^-CD38^-CD90^+CD34^+$, and/or progenitor cells expressing the markers $CD45^+Lin^-CD45RA^-CD38^-CD90^-CD34^+$.

Methods of Generating HMLPs

In the methods disclosed herein, HMLPs are generated by reprogramming endothelial cells (ECs) to provide reprogrammed, endothelial cell-derived HMLPs (rEC-HMLPs, also referred to herein as HMLPs). As used herein. "reprogramming" refers to a genetic process whereby differentiated somatic cells are converted into de-differentiated cells having a higher potency than the cells from which they were derived. ECs are reprogrammed by forcing the cells to express specific transcription factors that alter the differentiation state of the cells into a hematopoietic progenitor cell type.

Endothelial cells that can be used to generate HMLPs include mature ECs (e.g., neonatal, fetal, and adult ECs), and endothelial progenitor cells (EPCs). Exemplary sources of ECs include human dermal microvascular ECs (HDMECs) from adult dermis or neonatal foreskin, human umbilical vein/cord blood ECs (HUVECs), human umbilical artery ECs (HUAECs), human aortic ECs (HAoECs), human coronary artery ECs (HCAECs), human pulmonary artery ECs (HPAECs), human saphenous vein ECs (HS-VECs), human dermal blood ECs (HDBECs), human dermal lymphatic ECs (HDLECs), human bladder micro-vascular ECs (HBMECs), human cardiac micro-vascular ECs (HCMECs), human pulmonary micro-vascular ECs (HPMECs), human uterine micro-vascular ECs (HUMECs), human brain micro-vascular ECs (HBMECs) and fetal placental microvascular ECs (HPMECs). These cells are Von Willebrand factor (vWF) positive, CD31 positive, CD144 positive, smooth muscle alpha-actin (SMA) negative. Fetal microvascular ECs are further defined as fetal microvascular cells having the markers $CD34^+CD133^+VEGFR2^+CD45^-$ (see, Sölder E. et al., *Microvasc. Res.* 84:65-73 (2012)). Endothelial progenitor cells include those progenitor cells capable of differentiating to mature endothelial cells and characterized by $CD34^+VEGFR2^+$ and also possibly $CD133^+CD45^-$ (Urbich C. and Dimmeler S., *Circ. Res.* 95:343-353 (2004)). In a preferred embodiment, the ECs are HUVECs or hDMECs.

ECs used in the invention may be allogeneic (derived from a donor that is genetically similar, but not identical, to a recipient that is to receive reprogrammed cells, e.g., of the same species), syngeneic (derived from a donor that is genetically identical, or closely related, to a recipient that is to receive reprogrammed cells), or autologous (donor and recipient are the same individual).

Reprogramming Factors

Expression (including overexpression and forced expression) of transcription factors (TFs) herein identified can reprogram ECs to HMLPs. Expression of at least FOSB, GFI1, RUNX1, and SPI1 (these four factors collectively referred to herein as "FGRS" or "reprogramming factors"), or their respective functional homologs or functional derivatives, is required to generate HMLPs from ECs.

FOSB (Finkel-Biskis-Jinkins murine osteosarcoma viral oncogene homolog B) is a leucine zipper protein that dimerizes with proteins of the JUN family to form the transcription factor complex AP-1. FOSB is also known as AP-1, GOS3, GOS3, or GOSB. FOSB has at least six splice variant isoforms. As an example, the sequence for a specific human FOSB variant, FOSB isoform 1, is set forth in GenBank Accession No. CAG46898.

GFI1 (Growth factor independent 1 transcription repressor) is a member of a family of nuclear zinc finger proteins that function as transcriptional repressors. GFI family zinc-finger repressors form heterotrimeric complexes such as EHMT2-GFI1-HDAC1, AJUBA-GFI1-HDAC1, and RCOR-GFI-KDM1A-HDAC that repress via histone de-acetylase recruitment a number of genes responsible for specification of multi-lineage blood blood cell development. GFI1 is also known as SCN2, GFI-1, GFI1A, and ZNF163. There are at least four known splice variant isoforms of GFI1. As an example, the sequence for a specific human GFI1 variant, isoform 1, is set forth in GenBank Accession No. AAH32751.

RUNX1 (Runt-related transcription factor 1) is the alpha subunit of the core binding factor (CBF), a heterodimeric transcription factor that binds to the core element of many enhancers and promoters. The RUNX family comprises a number of CBF binding TFs such as RUNX2, RUNX3, CBFB, CEBP/Z, NFY/B, NFA/A, NFY/C, and RBPJ. There are at least three splice variant isoforms of RUNX1. RUNX1 is also known as AML1, AML1-EVI-1, AMLCR1, CBFA2, EVI-1, and PEBP2aB. As an example, the sequence for a specific human RUNX1 variant, isoform 1, is set forth in GenBank Accession No. AAI36381.

SPI1 (Spleen focus forming virus (SFFV) proviral integration oncogene) is an ETS domain transcription factor. SPI1 belongs to a family of ETS-domain encoding transcription factors that includes SPIE, ETV6, ETS1, ETV2, and ERG. There are at least three splice variants of SPIT. SPI1 is also known as hCG_25181, OF, PU.1, SFPI1, SPI-1, and SPI-A. As an example, the sequence for a specific human SPI1 variant, isoform 1, is set forth in GenBank Accession No. EAW67924.

Functional derivatives and homologs of the transcription factors specifically referenced herein are further contemplated for use in the disclosed methods. As used herein, a "functional derivative" is a molecule which possesses the capacity to perform the biological function of a TF disclosed herein, i.e, a molecule that is able to functionally substitute for the disclosed TF, e.g., in the reprogramming of ECs to HMLPs. Functional derivatives include fragments, parts, portions, equivalents, analogs, mutants, mimetics from natural, synthetic or recombinant sources including fusion proteins. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. Additions to amino acid sequences include fusions with other peptides, polypeptides or proteins.

A variant of a molecule is meant to refer to a molecule substantially similar in structure and function to either the entire molecule, or to a fragment thereof. Thus, as the term variant is used herein, two molecules are variants of one another if they possess a similar activity even if the structure of one of the molecules is not found in the other, or if the sequence of amino acid residues is not identical. The term variant includes, for example, splice variants or isoforms of a gene. Equivalents should be understood to include reference to molecules which can act as a functional analog or agonist. Equivalents may not necessarily be derived from the subject molecule but may share certain conformational similarities. Equivalents also include peptide mimics.

A "homolog" is a protein related to a second protein by descent from a common ancestral DNA sequence. A member of the same protein family (for example, the FOS family, the GFI family, the SPI family, or the RUNX family) can be a homolog. A "functional homolog" is a related protein or fragment thereof that is capable of performing the biological activity of the desired gene, i.e, is able to functionally substitute for the disclosed TF in the reprogramming of ECs to HMLPs. Homologs and functional homologs contemplated herein include, but are not limited to, proteins derived from different species.

A functional derivative or homolog can have 75%, 80%, 85%, 90%, 95% or greater amino acid sequence identity to a known FOSB, GFI1, RUNX1, or SPI1 amino acid sequence, or 75%, 80%, 85%, 90%, 95% or greater amino acid sequence identity to a FOSB, GFI1, RUNX1, or SPI1 family member or variant thereof. A FOSB functional derivative or homolog can have, for example, 75%, 80%, 85%, 90%, 95% or greater amino acid sequence identity to GenBank Accession No. CAG46898. A GFI1 functional derivative or homolog can have, for example, 75%, 80%, 85%, 90%, 95% or greater amino acid sequence identity to GenBank Accession No. AAH32751. A RUNX1 functional derivative or homolog can have, for example, 75%, 80%, 85%, 90%, 95% or greater amino acid sequence identity to GenBank Accession No. AAI36381. An SPI1 functional derivative or homolog can have, for example, 75%, 80%, 85%, 90%, 95% or greater amino acid sequence identity to GenBank Accession No. EAW67924.

Other TFs can be used in addition to the FGRS reprogramming factors. For example, any one or more of the following TFs can be used in addition to FGRS: ZPF36 (zinc finger protein tristetraprolin), FOS (FBJ murine osteosarcoma viral oncogene homolog), JUNB (jun B proto-oncogene), GMFG (glia maturation factor, gamma), KLF2 (Kruppel-like factor 2), NFE2 (nuclear factor, erythroid 2), KLF1 (Kruppel-like factor 1), KLF4 (Kruppel-like factor 4), LYL1 (lymphoblastic leukemia derived sequence 1), LMO2 (LIM domain only 2), TALI (T-cell acute lymphocytic leukemia 1), GATA1 (GATA binding protein 1), IKZF1 (IKAROS family zinc finger 1), GFI1B (growth factor independent 1B transcription repressor), VAV2 (vav 2 guanine nucleotide exchange factor), MEIS1 (Meis homeobox 1), MYB (v-myb avian myeloblastosis viral oncogene homolog), MLLT3 (myeloid/lymphoid or mixed-lineage leukemia (trithorax homolog, Drosophila); translocated to, 3), HLF (hepatic leukemia factor), BEX1 (brain expressed, X-linked 1), BEX2 (brain expressed, X-linked 2), and/or PBX1 (pre-B-cell leukemia homeobox 1), or functional derivatives or homologs of any of these TFs.

Vectors for Expression of Reprogramming Factors

Expression of the reprogramming factors FGRS is effected by introduction of exogenous nucleic acids into an EC to drive expression of the desired factors in the EC. Each reprogramming factor can be introduced into the EC as a polynucleotide transgene within a vector that encodes the reprogramming factor operably linked to a heterologous promoter that can drive expression of the polynucleotide in the EC.

Many vectors useful for transferring exogenous genes into target mammalian cells are available. The vectors may be episomal, e.g. plasmids or virus derived vectors such cytomegalovirus vector, adenoviral vector, adeno-associated viral (AAV) vector, etc., or the vectors may be integrative, e.g., integrating the reprogramming gene into the target cell genome, through homologous recombination or random integration, e.g. retrovirus derived vectors such MMLV (Moloney Murine Leukemia Virus), HIV-1, ALV (Avian leukosis virus), or lentiviral vectors. In a specific embodiment, the vector is a lentiviral vector.

In one embodiment, a vector for expressing the reprogramming factor comprises a promoter operably linked to the reprogramming factor gene. The phrase "operably linked" or "under transcriptional control" as used herein means that the promoter is in the correct location and orientation in relation to a polynucleotide to control the initiation of transcription by RNA polymerase and expression of the polynucleotide. Several promoters are suitable for use in the vectors for expressing the reprogramming factor, including, but not limited to, RNA pol I promoter, RNA pol II promoter, RNA pol III promoter, and cytomegalovirus (CMV) promoter. Other useful promoters are discernible to one of ordinary skill in the art. In some embodiments, the promoter is an inducible promoter that allows one to control when the reprogramming factor is expressed. Suitable examples of inducible promoters include tetracycline-regulated promoters (tet on or tet off) and steroidregulated promoters derived from glucocorticoid or estrogen receptors. Constitutive expression of TFs can be achieved using, for example, expression vectors with a CMV, CAG (chicken beta-actin promoter with CMV enhancer), or PGK (phosphoglycerate kinase 1) promoter. Inducible expression of TFs can be achieved using, for example, a tetracycline responsive promoter, such as the TRE3GV (Tet-response element 3rd generation) inducible promoter (Clontech Laboratories, Mountain View, Calif.). Alternatively, the promoter operably linked to the transgene may be a promoter that is activated in specific cell types and/or at particular points in development.

Depending on the promoter used, expression of any one, or all, of the FGRS reprogramming factors can be constitutive (continuous expression of the factor) or inducible (capable of being turned on and off). Expression can also be transient, that is, temporary expression of the reprogramming gene of interest in ECs over a limited time span. Transient expression may be achieved by use of a non-integrative vector, where the vector is lost from the cell or cell population over time, or by use of an inducible promoter in an integrative or non-integrative vector that can be manipulated to cease expression of the reprogramming gene after a period of time. In a specific embodiment, transient expression of one or more of the FGRS reprogramming factors is employed to generate expression for no more than three days, no more than five days, no more than 10 days, or no more than one, two, or three weeks.

Suitable vectors can contain markers to identify and/or select transformed cells. Examples of selectable markers include visual markers such as green fluorescent protein (GFP), red fluorescent protein (RFP), or fluorescein; epitope markers such as His, c-myc, GST, Flag, or HA tags; enzymatic/nutritional markers such as DHFR (dihydrofolate reductase); or antibiotic resistance markers such as neomycin, puromycin, blasticidin, or hygromycin.

Transformation of Endothelial Cells with Reprogramming Factors

Any suitable means of transfecting or transducing endothelial cells with reprogramming factors can be used. For various techniques for transformation or transfection of mammalian cells, see Keown et al., 1990, Methods Enzymol. 185: 527-37; Sambrook et al., 2001, Molecular Cloning, A Laboratory Manual, Third Edition, Cold Spring Harbor Laboratory Press, N.Y. Vectors carrying FOSB, GFI1, RUNX1, and SPI1 can be transfected into cells using standard methods known in the art, including, but not limited to, liposome-mediated transfection, polybrene-mediated transfection, DEAE dextran-mediated transfection, electroporation, calcium phosphate precipitation, microinjection, or micro-particle bombardment. Similarly, FOSB, GFI1, RUNX1, and SPI1 can be delivered to endothelial cells using a viral delivery system such as lentivirus, adenovirus, retrovirus, adeno-associated virus or herpesvirus delivery system. In a preferred embodiment, ECs are transfected by one, two, three, or four lentiviral vectors driving expression of FOSB, GFI1, RUNX1, and SPIT.

ECs expressing one, two, three, or all four of the FGRS reprogramming factors can be enriched in the population by selecting for cells expressing markers indicative of transformed cells. For example, each reprogramming factor can be placed in a separate vector with a distinct selection marker (e.g., vectors can provide resistance to different antibiotics, different visual markers, and/or different nutritional markers). By selection for each marker representing transformation with the different vectors, the population of ECs transformed with all four factors can be increased. In a specific example, distinct vectors, with each vector encoding a different reprogramming factor, are marked by antibiotic resistance or green fluorescent protein (AT), respectively.

Culture Conditions for EC Reprogramming

ECs transformed with FGRS are preferably cultured with minimal or no serum in the culture media ("serum-free" media). The presence of serum in the media has been found by the inventors to reduce production of HMLPs. Transformed ECs can be cultured in serum-free media suitable for culture and expansion of heniatopoietic cells. Such media can be based, for example, on Iscove's Modified Dulbecco's Medium (IMDM) or other suitable culture media, and can include supplements such as standard bovine serum albumin, insulin, 2-mercaptoethanol, and/or transferrin (for example, STEMSPAN SFEM, Stemcell Technologies, Vancouver, Canada). Additional supplements can include a serum replacement supplement with a defined formulation for growth of undifferentiated cells, for example, KNOCK-OUT serum replacement (GIBCO). ECs can be cultured for three days, five days, ten days, twelve days, one week, two weeks, or three weeks or more, to reprogram the ECs into HMLPs.

Additional media supplements for achieving EC reprogramming can include growth factors and/or cytokines, such as 2-8 ng/ml bFGF, 5-15 ng/ml EGF, 15-25 ng/ml SCF, 15-25 ng/ml FLT3, 15-25 ng/ml TPO, 15-25 ng/ml IGF-1, 5-15 ng/ml IGF-2, 5-15 ng/ml IL-3, and/or 5-15 ng/ml IL-6. In a preferred example, the culture media includes 2-8 ng/ml bFGF, 5-15 ng/ml EGF, 15-25 ng/ml SCF, 15-25 ng/ml FLT3, 15-25 ng/ml TPO, and 5-15 ng/ml IL-6.

Endothelial Feeder Cells

ECs expressing at least the FGRS factors are cultured with endothelial feeder cells. These feeder cells provide an AGM-like (aorta-gonad-mesonephros-like) niche environment that resembles the physiological environment in which EC programming occurs. Preferably, endothelial feeder cells are grown to form a confluent monolayer on the bottom of the tissue culture vessel, and then the culture vessel is seeded with transformed ECs. Any endothelial cell can be used as a feeder cell, such as mature ECs (e.g., neonatal, fetal, and adult ECs), and endothelial progenitor cells (EPCs). Exemplary sources of ECs include human dermal microvascular ECs (hDMECs) from adult dermis or neonatal foreskin, human umbilical vein/cord blood ECs (HUVECs), and fetal placental microvascular ECs (hPMECs). In a preferred embodiment, HUVECs are used as endothelial feeder cells.

Feeder cells are preferably able to grow and survive in a serum-free environment to enable culturing with ECs in serum-free media. Many types of endothelial cells cannot be maintained in culture in the absence of serum. Modification of endothelial cells to enable survival and proliferation for use as feeder cells in a serum-free culture can overcome this barrier in endothelial cells that would otherwise require serum.

Endothelial cells can be modified, for example, by transformation of cells with genes that drive growth and proliferation in the absence of serum. Examples of genes that support survival of endothelial cells in culture without serum include the Akt (protein kinase B or PKB) gene and the adenovirus E4ORF1 gene. In a specific embodiment, HUVECs are transformed to express a gene selected from Akt or the adenovirus E4ORF1 gene. Transformation of HUVECs with E4ORF1 is disclosed in U.S. Pat. No. 8,465,732, the contents of which are incorporated herein by reference. Transformation of HUVECs with Akt is disclosed, for example, in Fujio and Walsh, *J. Biol. Chem.* 274:16349-16354 (1999), the contents of which are incorporated herein by reference.

Any suitable means of transfecting or transducing endothelial cells with genes that promote survival and proliferation in a serum-free environment can be used. For example, the E4ORF1 or Akt gene can be transfected into cells using standard methods known in the art, including, but not limited to, liposome-mediated transfection, polybrene-mediated transfection, DEAE dextran-mediated transfection, electroporation, calcium phosphate precipitation, microinjection, or micro-particle bombardment. Similarly, the E4ORF1 or Akt gene can be delivered to endothelial cells using a viral delivery system such as lentivirus, adenovirus, retrovirus, adeno-associated virus or herpesvirus delivery system. In an embodiment, the E4ORF1 or Akt gene is delivered to endothelial cells using a lentiviral gene delivery system.

Feeder cells can be cultured in endothelial growth media (for example, Medium 199, Thermo Scientific: #FB-01), with 10-30% Fetal Bovine Serum (Omega Scientific), 15-25 µg/ml endothelial cell supplement (available, for example, from Biomedical Technologies: #BT-203), 0.5-2× Pen/Strep, and 15-25 units/ml Heparin (for example, Sigma: # H3149-100KU). The feeder cells can be plated in a layer on the surface of a culture vessel and, preferably once a confluent layer of feeder cells is established on the culture vessel, the endothelial growth medium is replaced with serum-free medium, and ECs expressing reprogramming factors can be plated on top of the feeder layer.

For example, mature HUVECs (or hDMECs) can be transduced with the FGRS reprogramming factors and then, 2-3 days later, washed and re-plated on established monolayers of E4-HUVEC feeders. Transduction of $5 \times 10^4$ mature ECs can generate multiple distinct colonies of HMLPs during serum-free co-culture with E4-HUVECs.

Isolation of HMLPs from Culture

HMLPs can be isolated from culture for further use. In one embodiment, HMLPs are isolated by isolating CD45+ cells. In another embodiment, HMLPs are isolated by isolating CD45+CD34+ cells. HMLPs can be isolated, for example, by cell sorting and separation of CD45+ cells from a co-culture of HMLPs with endothelial feeder cells (which are CD45−).

HMLPs can be isolated from culture as a heterogenous/mixed population (e.g., a population of cells where different cells in the population express distinct markers aside from expression of CD45+ or CD45+CD34+), or as a relatively homogenous/substantially pure population (e.g., a population of cells where greater than 50%, greater than 60%, greater than 70%, greater than 75%, greater than 80%, greater than 85%, greater than 90%, greater than 95%, or greater than 98% of the cells express a common set of markers in addition to expression of $CD45^+$ or $CD45^+CD34^+$).

Pharmaceutical Compositions and Methods of Treatment

This disclosure further provides pharmaceutical compositions of EC-generated HMLPs with a pharmaceutically acceptable carrier. Such a pharmaceutical composition may contain in addition to the cells a physiologically acceptable matrix or a physiologically acceptable vehicle. The type of matrix and/or vehicle will depend among other things on the intended route of administration. Suitable matrices and/or vehicles are known in the art. Such compositions can be frozen and stored, for example, in liquid nitrogen, using established methods for storing stem cells or cord blood cells. In a preferred example, pharmaceutical compositions are provided for intravenous infusion into a patient.

Further provided are methods of treatment utilizing the EC-generated HMLPs and pharmaceutical compositions disclosed herein. HMLPs provided herein are suited for reconstituting hematopoietic cells in a subject or for providing cell populations enriched in desired hematopoietic cell types. The HMLPs of the present invention can be used for reconstituting the full range of hematopoietic cells in an immunocompromised subject following therapies such as, but not limited to, radiation treatment and chemotherapy. Administration of the disclosed HMLPs, such as by infusion or transplantation into a subject, can augment or replace stem or progenitor cells of the liver, pancreas, kidney, lung, nervous system, muscular system, bone, bone marrow, thymus, or spleen. HMLP transplants can be autologous or allogenic, including matched and mismatched HLA type hematopoietic transplants. It is appreciated that it may be necessary to treat the host to reduce immunological rejection of the donor cells.

The subject or individual can be any animal in need of cell-based therapy. In some embodiments, the individual is a mammal. Mammals include, but are not limited to, humans, non-human primates, mice, cows, horses, dogs, cats and the like. In a preferred embodiment, the mammal is a human.

With respect to administering the expanded cells provided herein to a patient, an effective amount of expanded cells may range from as few as several hundred or fewer to as many as several million or more. It will be appreciated that the number of expanded cells to be administered will vary depending on the specifics of the disorder to be treated, including but not limited to size or total volume to be treated, as well as the needs and condition of the recipient, among other factors familiar to the medical professional. In some embodiments, between $10^3$ and $10^{10}$ cells per 100 kg person are administered or transplanted into the subject or individual. Methods of administering or transplanting are well known in the art and include, for example, infusion. Expanded cells provided herein can be administered, for example, by intravenous infusion.

In one embodiment, HMLPs are used to augment or replace bone marrow cells in bone marrow transplantation. Human autologous and allogenic bone marrow transplantations are currently used as therapies for diseases such as leukemia, lymphoma and other life-threatening disorders. The drawback of these procedures, however, is that a large amount of donor bone marrow must be removed to insure that there are enough cells for engraftment. The present invention reduces or eliminates the need for large bone marrow donation, by substituting or supplementing a marrow donation with EC-generated HMLPs for infusion or transplantation into a recipient.

In some embodiments, a single administration of cells is provided. In other embodiments, multiple administrations are used. Multiple administrations can be provided over periodic time periods such as an initial treatment regime of 3 to 7 consecutive days, and then repeated at other times.

EXAMPLES

Cell Culture

Human umbilical vein endothelial cells (HUVECs) were obtained as described in Goldberg, A. D. et al., (Cell) 140:678-691 (2010). HUVECs were cultured in Endothelial Growth Media (EM): Medium 199 (Thermo Scientific:

FB-01), 20% Fetal Bovine Serum (Omega Scientific), 20 µg/ml endothelial cell supplement (Biomedical Technologies: #BT-203), 1× Pen/Strep, and 20 units/ml Heparin (Sigma: # H3149-100KU). Adult primary human dermal microvascular endothelial cells (hDMEC) were purchased from ScienCell Research Laboratories (cat #2020). Serum-free hematopoietic media was made of StemSpan SFEM (Stemcell Technologies), 10% KnockOut Serum Replacement (Invitrogen), 5 ng/ml bFGF, 10 ng/ml EGF, 20 ng/ml SCF, 20 ng/ml FLT3, 20 ng/ml TPO, 20 ng/ml IGF-1, 10 ng/ml IGF-2, 10 ng/ml IL-3, 10 ng/ml IL-6 (all from Invitrogen, eBioscience, or Peprotech).

Purification of Human Cord Blood Progenitors.

Human umbilical cord blood was obtained under the IRB protocol "Stage Specific Differentiation of Hematopoietic Stem Cells into Functional Hemangiogenic Tissue" (Weill Cornell Medical College IRB #09060010445). Cord blood mononuclear cells were purified by density gradient using Ficoll-Paque (GE) and enriched for $CD34^+$ progenitors using magnetic separation using anti-CD34 microbeads (Miltenyi). Further purification was achieved by negative selection of Lin+ cells using Human Progenitor Cell Enrichment Kit (StemCell Technologies). RNA was extracted from $Lin^-CD34^+CD45^+$ cells isolated by FACS using Arcturus PicoPure RNA isolation kit (Applied Biosystems; this kit was used for all RNA extraction procedures).

Flow Cytometry.

Flow cytometry analysis was performed on a Becton Dickenson LSRII SORP, and fluorescence activated cell sorting (FACS) was performed on an Aria II SORP. Antibodies used were raised against human CD45, CD34, CD14, CD31, CD43, CD90, CD41a, CD33, CD19, CD3, CD4, CD8, CD235, CD45RA, CD83, CD11b, CD38, LIN cocktail, CD117, CD133, CD144 (BD Pharmingen, eBioscience) or mouse CD45 (eBioscience.) Voltage adjustments and compensation was performed with CompBeads (BD Pharmingen), and gating was performed on fluorophore minus one (FMO) controls and unstained controls.

Identification of Transcription Factors that are Differentially Expressed Between Endothelial Cells and Hematopoietic Progenitor Cells.

To identify the conditions that are essential for hematopoietic specification, we performed RNA-sequencing on freshly isolated HUVECs and $Lin^-CD34^+$ human cord blood hematopoietic progenitors to identify differentially expressed TFs. 26 differentially expressed TFs were identified (Table 1).

TABLE 1

Transcription Factors (TFs) that are differentially expressed between HUVEC and $Lin^-CD34^+$ human cord blood (CB) hematopoietic progenitor cells.

| TF | HUVEC | $CD34^+Lin^-(CB)$ |
|---|---|---|
| ZFP36 | 4.81 | 12.4 |
| FOS | 3.82 | 12.36 |
| JUNB | 6.26 | 12.17 |
| GMFG | 5.33 | 10.3 |
| KLF2 | 7.7 | 10.28 |
| FOSB | 1.51 | 10.28 |
| NFE2 | 0 | 9.45 |
| KLF1 | 0 | 9.29 |
| KLF4 | 0 | 9.22 |
| LYL1 | 8.55 | 9.03 |
| LMO2 | 7.24 | 8.87 |
| TAL1 | 6.2 | 8.31 |
| GATA1 | 0 | 8.18 |
| SPI1 | 0 | 8.04 |

TABLE 1-continued

Transcription Factors (TFs) that are differentially expressed between HUVEC and $Lin^-CD34^+$ human cord blood (CB) hematopoietic progenitor cells.

| TF | HUVEC | $CD34^+Lin^-(CB)$ |
|---|---|---|
| IKZF1 | 0 | 7.83 |
| GFI1B | 0 | 7.7 |
| VAV1 | 0 | 7.67 |
| MEIS1 | 3.23 | 6.75 |
| MYB | 0.23 | 6.47 |
| MLLT3 | 4.21 | 6.4 |
| RUNX1 | 0.21 | 6.23 |
| GFI1 | 0 | 5.54 |
| HLF | 0 | 4.67 |
| BEX1 | 2.52 | 4.47 |
| PBX1 | 4.24 | 4.88 |
| BEX2 | 0.03 | 3.95 |

Lentiviral Vectors.

Candidate transcription factors were subcloned into either pLVX-IRES-Zs Green1 lentivector (Clontech), pLOC lentivector (OpenBiosystems), or LV105 lentivector (Genecopoeia). Lentiviral particles were packaged as described in Sandler, V. M. et al., *PLoS One* 6:e18265 (2011). In brief, human embryonic kidney 293FT (HEK293FT) cells were co-transfected with a lentivector and two helper plasmids, psPAX2 and pMD2.G (Trono Lab through Addgene), in an equal molar ratio. Supernatant was collected 48-52 hours post-transfection, filtered and concentrated using Lenti-X concentrator (Clontech). Viral titers were determined in limiting dilution experiments using HUVECs as target cells. We used either the number of $GFP^+$ cells, or the number of formed colonies in the presence of selection antibiotics (puromycin) as a read-out for the number of infectious viral particles per volume. We used MOI 5-10 for infection of HUVECs or hES cells derived ECs and 10-25 for infection of fibroblasts.

HUVECs and HEFs (human embryonic fibroblasts) were transduced with lentivirus expressing SPI1 and expanded in the presence of puromycin (0.5 to 1 µg/ml) for 10-14 days to obtain sufficient number of cells. All four FGRS expressing lentiviruses were resuspended in endothelial cell culture media and applied to the feeder cells. 12-24 hours later transduced ECs were fed with additional EC culture media. 2-3 days later, post-transduction transduced ECs were re-plated on top of feeder cells.

We screened various combinations of the 26 identified TFs to identify those capable of reprogramming HUVECs to hematopoietic cells. To eliminate potential contamination of starting HUVEC cultures with hematopoietic cells, we sorted freshly isolated HUVECs to obtain mature $CD45^-CD133^-cKit^-CD31^+$ ECs (FIG. 1A). In the absence of exogenously expressed TFs, these HUVECs never give rise to $CD45^+$ hematopoietic cells. Therefore, we used the emergence of $CD34^+CD45^+$ cells as the initial readout to identify cells that acquired hematologic potential. Lentiviral vectors expressing identified TFs with either a green fluorescent protein (GFP) marker or puromycin resistant gene were used to transduce HUVECs (FIG. 1A). The transduced HUVECs were then propagated without serum in the presence of hematopoietic cytokines (TPO, KITL, FLT3L; see Methods). Approximately 2 weeks after transduction, HUVEC cultures revealed emergence of round $GFP^+CD45^+$ cells (FIG. 1B) and round grape-like colonies of $GFP^+CD45^+$ cells began to emerge from the endothelial monolayer (FIG. 1A. Day 12-16).

Identification of Necessary Transcription Factors for Reprogramming ECs.

Figure 1B:
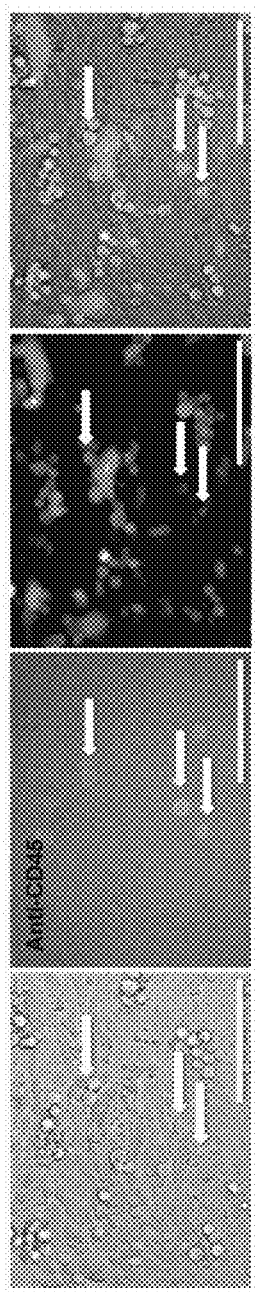
Figure 1C:
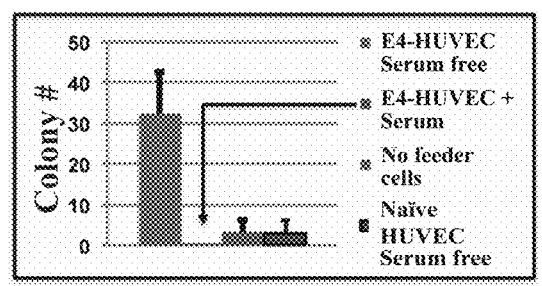
Figure 1D:
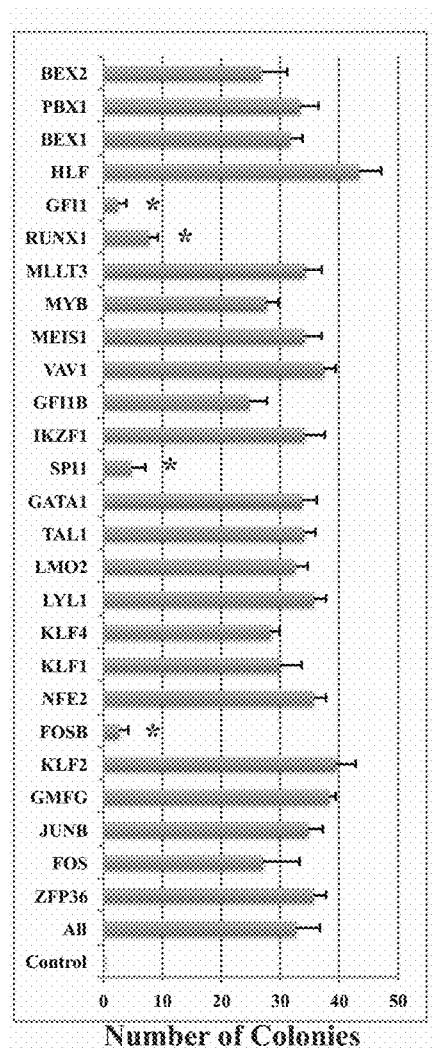
Figure 1E:
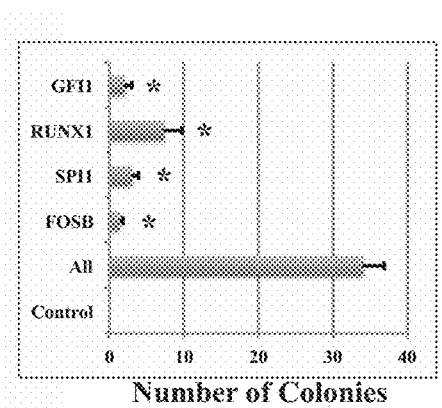

HUVECs were transformed with 25 TFs at a time, with each transformation lacking a different TF as identified in Table 1. This systematic "one-by-one dropout" of candidate TFs demonstrated that hematopoietic reprogramming required enforced expression of FOSB, GFI1, RUNX1, and SPI1 (this combination referred to as "FGRS") (FIG. 1D, n=3). The other candidate TFs were not required. We found that the FGRS TFs alone were sufficient for the generation of hematopoietic-like colonies (FIG. 1E, n=3). Removal of any one FGRS factor did not completely eliminate formation of hematopoietic-like clusters but significantly reduced the number of clusters (p<0.05) and the emerging hematopoietic-like cells did not actively divide.

Design of a Feeder Layer to Enhance and Sustain Growth of FGRS Transduced ECs.

ECs and HSPCs co-develop in the aorta-gonad-mesonephros (AGM) region. Because primitive HSCs require a suitable niche for expansion in the developing fetus, vascular niche feeder cells may enhance the survival and sustain the specification of the emerging hematopoietic-like cells. To test this hypothesis, we used an in vitro model of the vascular niche to enable serum- and growth factor-free culture of HUVECs by expression of the E4ORF1 gene of the adenovirus E4 complex (E4-HUVECs), as described by Butler, J. M. et al., (*Blood*) 120:1344-1347 (2012). Our group and others have shown that E4-HUVECs maintain their niche-like support for primitive hematopoietic cells, mouse cKit$^-$lin$^-$Sca1$^+$CD34$^-$Flt3$^-$ and human Lin$^-$CD45RA$^-$CD38$^-$CD34$^+$CD49f$^-$ HSPCs, which are able to engraft lethally irradiated primary and secondary recipients.

Using this vascular niche co-culture system, we devised a xenobiotic-free platform in which mature HUVECs (or hDMECs) were transduced with the FGRS reprogramming factors and then, 2-3 days later, washed and re-plated on established monolayers of E4-HUVEC feeders. Transduction of $5 \times 10^4$ mature HUVECs yielded 32.3±10.5 (n=8) distinct colonies during serum-free co-culture with E4-HUVECs but no colonies were observed if serum was added. Nave HUVECs were unsuitable as a vascular niche because they could not survive in serum-free culture for more than 1-2 weeks, preventing FGRS-ECs from benefiting from vascular niche support during reprogramming. Indeed, GFP$^+$ hematopoietic-like colonies emerging from co-cultures with naive HUVECs (3.4±3.2 colonies per $5 \times 10^4$ transduced HUVEC; n=5) were no more common than outgrowth from FGRS-ECs in the absence of feeder cells.

E4-HUVECs provide a necessary environment to culture FGRS-ECs. Co-culture of FGRS transduced ECs (FGRS-ECs) with E4-HUVECs significantly increased the yield and persistence of the hematopoietic-like colonies which ultimately manifested morphological and molecular features of rEC-HMLPs. Thus, efficient generation of hematopoietic cells from FGRS-ECs required long-term supportive signals from ECs with niche-like function.

For these reasons, we used the E4-HUVEC, vascular niche feeder platform for further characterization of the hematopoietic reprogramming of FGRS transduced ECs. Transduction of $5 \times 10^4$ ECs for 2 days and subsequent co-culture with E4-HUVECs for 3 weeks, resulted in the emergence of 32.3±10.5 (n=8) distinct colonies (FIG. 1C). These data suggest that the supportive vascular cells are essential for emergence of the hematopoietic cells from FGRS transduced ECs.

Confirmation of Expression of FGRS TFs in Cultured Cells.

Without accounting for the proper stoichiometry of the FGRS that were introduced into the nave ECs the efficiency of reprogramming was very low and approached to less than 0.07%. Therefore, to improve the efficiency of reprogramming, we developed a strategy to select those subsets of FURS transduced ECs that were transduced with a proper stoichiometry of the TFs. We initially focused on generating ECs with proper stoichiometry of GFI1, SPI1 and FOSB TFs, because their native expression in ECs is negligible (see Table 1). To do this, we transduced $5 \times 10^6$ ECs with FGRS lentiviral. "cocktail" marked by puromycin resistance (SPIT) or (HT (FOSB and GM). We then applied puromycin selection for 2 days to enrich Mt-expressing cells and sorted them for GFP expression to enrich for SPI1$^+$GFP$^+$ (FOSB/GFI1) ECs. We then seeded these GFP$^+$ cells into 12-well plates and expanded them for two days in serum-free culture ($10^5$ cells per plate, n=3).

We then re-plated $10^4$ of the GFP$^+$ puromycin resistant cells on an E4-HUVEC feeder layer in hematopoietic media and quantified the number of hematopoietic clusters after ~20 days of co-culture. We found that these GFP$^+$, puromycin resistant cells yielded 156.0±3.6 (n=3) hematopoietic-like colonies per $10^4$ re-plated cells suggesting that the efficiency of reprogramming was at least 1.5%. This calculation assumes that each colony originates from a single reprogrammed cell and that the transduced ECs—that we know express two of the factors (SPI1 and either/both FOSB or GFI1)—each express all four FGRS TFs. The efficiency is likely much higher in cells expressing the appropriate stoichiometric quantities of each factor. Therefore, it is highly unlikely that our reprogramming approach is due to spontaneous differentiation of a very scarce pre-existing population of hemogenicthemangiohlastic ECs present within the UUVEC monolayers.

A Supportive Vascular Niche Facilitates Reprogramming of FGRS-ECs into Proliferating Multi-Lineage, Erythroid-Megakaryocytic-Myeloid Progenitors.

Figure 2A:
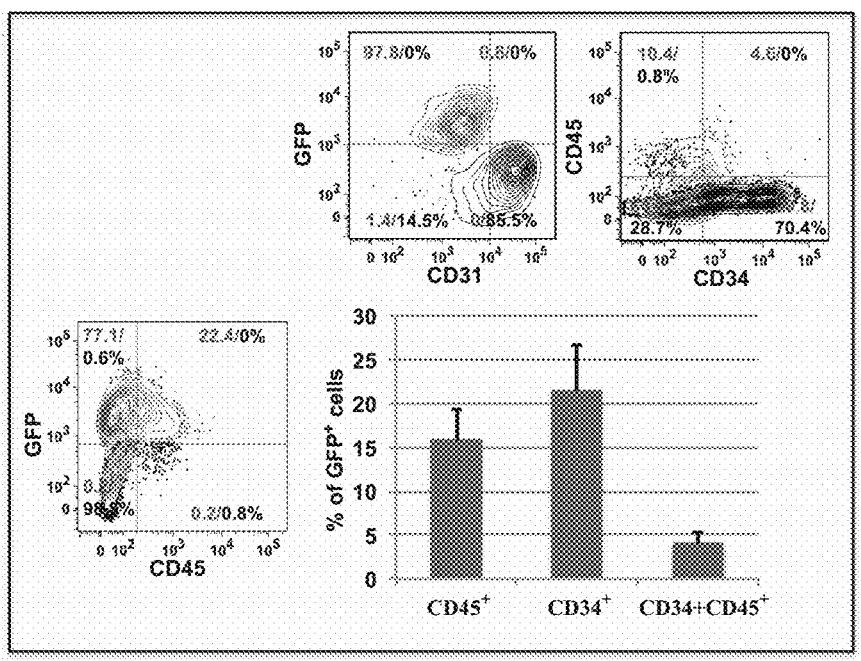
FIGS. 2A-2E. A. FACS analysis of the mixed GFP E4-HUVECs feeder vascular monolayer and $GFP^+$ FGRS transduced HUVECs shows that $GFP^+$ nascent hematopoietic cells lose expression of CD31 (a mature endothelial cell marker) and acquire $CD45^+$ and $CD45^+TD34^+$ hematopoietic phenotype. Percentages in the dot-plots in grey font refer to the gate in the upper left-hand dot-plot ($GFP^+$ cells). Percentages in the dot-plots in black font refer to $GFP^-$ cells. B. Immunophenotypic analysis of FGRS reprogrammed HUVECs. Emerging hematopoietic cells were tested for expression of lineage markers, CD45RA, CD45, CD34, CD90, and CD38. Two populations of $CD45^+Lin^-CD45RA^-CD38^-CD90^+CD34^+$ and $CD45^+Lin^-CD45RA^-CD38^-CD90^-CD34^+$ cells, satisfying the phenotypic criteria for hematopoietic stem-like cells or multi-potent progenitors respectively, are shown. C. At the end of the Phase I, four weeks after FGRS transduction and vascular-niche induction, GFPCD45CD34 cells were sorted and seeded for CFU assays. Typical hematopoietic colonies arose in the CFU assay (magnification ×4); wide field (left column) and corresponding fluorescent images (right column). Top to bottom: granulocytic-erythroid-monocytic-megakaryocytic (GEMM), Erythroid/Myeloid, and granulocytic-macrophage (GM) colonies. Lower panel images show hemoglobinized colonies. The graph shows quantification of the CFU assay. D. Wright-Giemsa stain of a cytospin of cells obtained from the CFU assay colonies confirmed lineage specification of differentiating rEC-HMLPs (magnification ×60). We detected cells with typical morphological features of erythroid, macrophage, granulocyte, and megakaryocyte precursors. E. Immunophenotypic analysis of cells grown in the CFU assay revealed the presence of $CD235^+$, $CD11b^+$, $CD14^+$, $CD83^+$, and $CD45^+$ cells, suggesting that rEC-HMLPs differentiated into erythroid, macrophage, monocyte, and dendritic cell progenies.

Within three to four weeks of co-culturing with E4-HUVECs, FGRS-ECs began to rapidly proliferate and form GFP$^+$ grape-like clusters partially attached to E4-HUVEC monolayers. Wright-Giemsa staining of the grape-like clusters revealed cells morphologically reminiscent of hematopoietic progenitors and their progeny (FIG. 1B, right panel). We occasionally also observed formation of large multi-colony niche-like structures that physically separated developing hematopoietic colonies from their surroundings (n=4). Flow cytometry showed that most FGRS-EC progeny (GFP$^+$ cells) lost expression of the mature EC marker, CD31, and a subset acquired expression of the pan-hematopoietic marker CD45, sometimes in conjunction with co-expressed CD34 (FIG. 2A, n=9). In contrast, the GFP$^+$ E4-HUVEC retained high-level CD31 expression and remained CD34$^+$CD45$^-$. A subset of GFP$^+$CD45$^+$ FGRS-EC progeny expressed other hematopoietic markers, such as CD43$^+$ (8.96%±2.3; n=3), CD90$^+$ (Thy-1$^+$) (6.15%±1.13; n=3), and CD14$^+$ (40.0%±4.95; n=3). Proliferation of GFP$^+$ cells increased near the end of a four to five week co-culture with E4-HUVEC, resulting in the generation of up to $20 \times 10^6$ GFP$^+$CD45$^+$ cells, approximately a 400 fold expansion of the input ECs (FIG. 3A; $17.2 \times 10^6$±2.4; n=6). Three to five days later both the rate of proliferation and the number of viable cells rapidly declined, although generation of GFP$^+$CD45$^+$ continued at a diminished rate. Therefore, a supportive vascular niche of E4-HUVEC cells facilitates reprogramming of FGRS-ECs into proliferating multi-lineage, erythroid-megakaryocytic-myeloid progenitors (rEC-HMLPs).

rEC-HMLPs can Generate Erythroid, Macrophage, Granulocyte, and Megakaryocyte Precursor Cells.

Figure 2B:
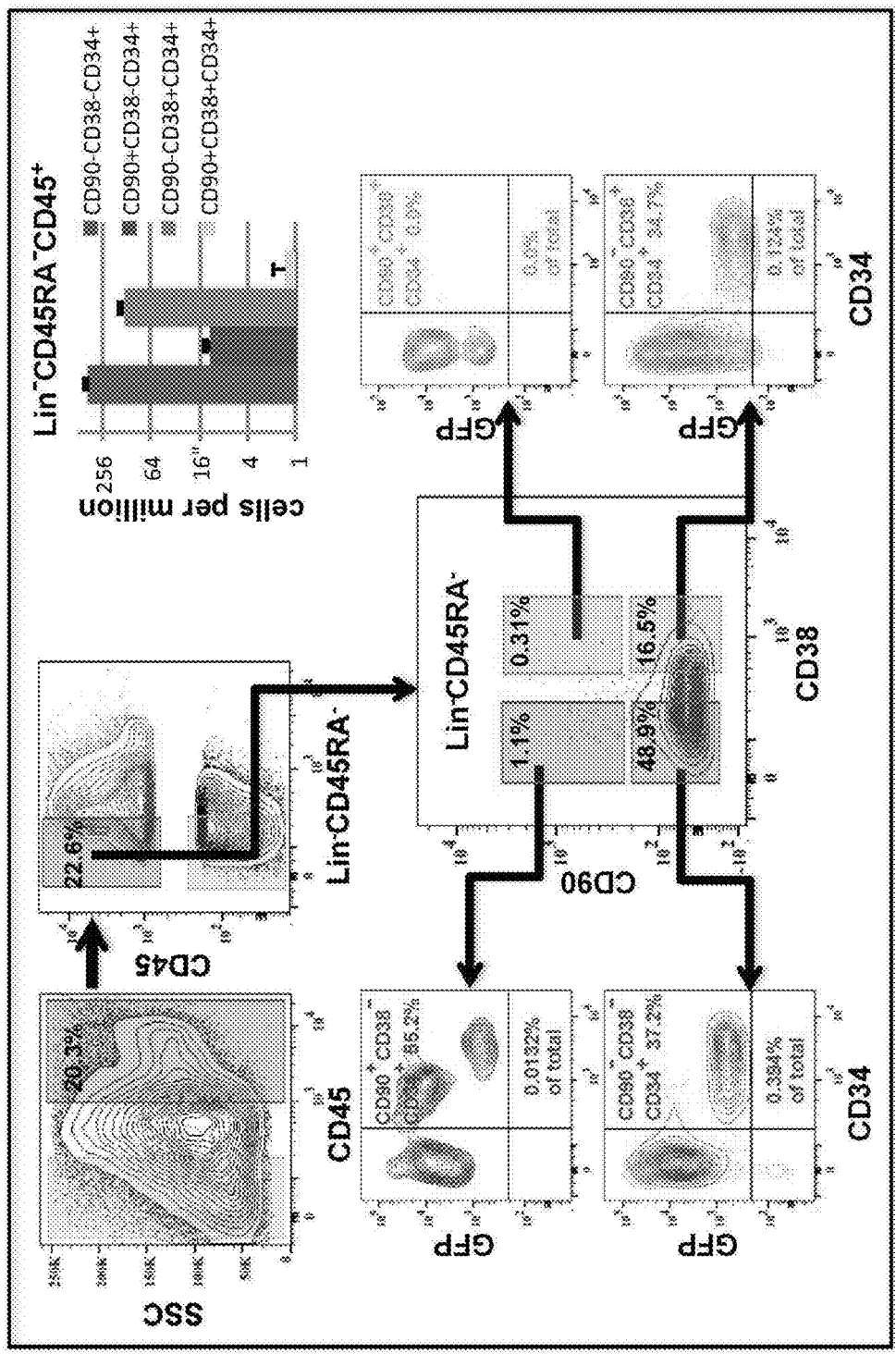
Figure 2C:
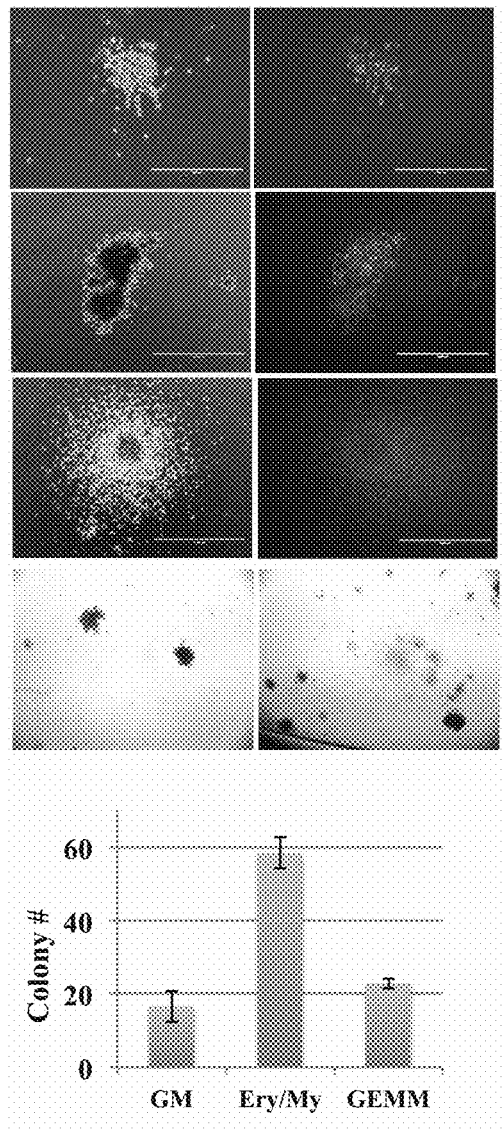
Figure 2D:
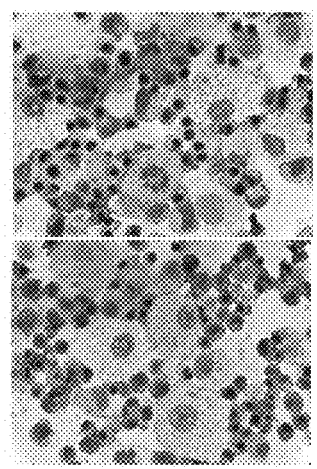

To assess the functionality of rEC-HMLPs, we conducted colony forming unit (CFU) assays using standard methylcellulose assays. If HUVECs were indeed converted into functional rEC-HMLPs then these cells should be able to differentiate into at least two distinct hematopoietic lineages in the CFU assay. Four weeks after transduction of HUVECs with FGRS and vascular niche co-culture, GFP-FCD45+CD34+rEC-HMPLs were sorted and seeded at the density of 1200-1600 cells/cm$^2$ (5000-7000 cells/35 mm plate) for CFU assays (n=3). Within 14 days the cells gave rise to GFP cell aggregations morphologically resembling CFU-GM (granulocyte/macrophage colony forming units), CFU-GEMM (granulocyte/erythrocyte/monocyte/megakaryocyte colony forming units), and partially hemoglobinized BFU-E type hematopoietic colonies (burst forming unit-erythroid, an erythroid progenitor type) (FIG. 2C). Lineage specification in the CFU assay was verified by staining the colonies with Wright-Giemsa (FIG. 2D). We were able to detect cells with typical morphological features of erythroid, macrophage, granulocyte, and megakaryocyte precursors as defined in Beutler, E., ed., *Williams Hematology*; McGraw Hill, Inc. (Fifth Edition, 1995).

Figure 2E:
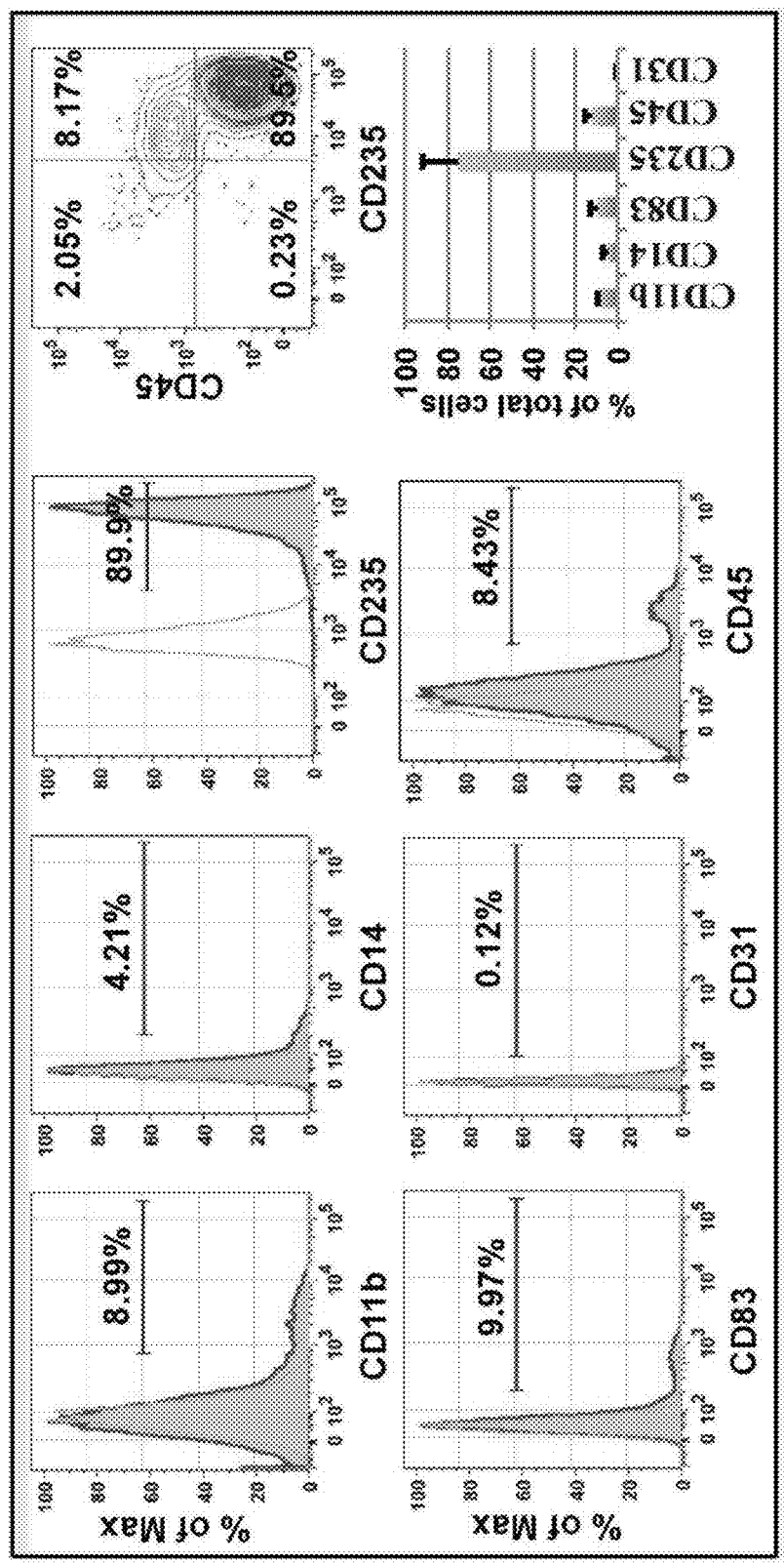

Immunophenotypic analysis of the colonies obtained from methylcellulose cultures revealed the presence of CD235, CD11b, CD14, CD83, and CD45 cells suggesting that rEC-HMLPs differentiated into erythroid, macrophage, monocyte, and dendritic cell progeny. CD235$^+$ (Glycophorin A) cells were also CD45$^-$ suggesting erythroid differentiation (FIG. 2E).

Human Adult Dermal Micro-Vascular Endothelial Cells are Capable of Forming Autologous HSCs.

Figure 4A:
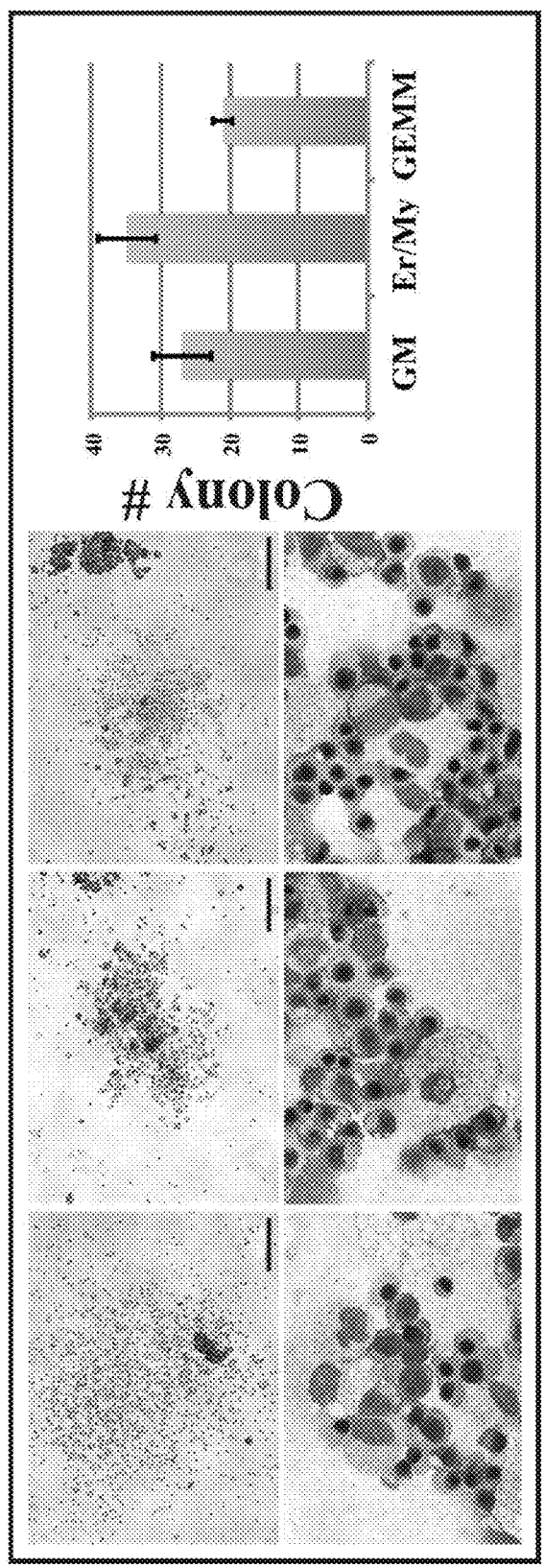
FIGS. 4A-4F. A. Schematic representation of in vitro and in vivo functional tests of hDMEC-derived rEC-HMLPs. At the end of the Phase I, four weeks after FGRS transduction, rEC-HMLPs were sorted and seeded for CFU assays. Typical hematopoietic colonies arose in the CFU assay (scale bar is 200 µm); wide field (upper row). Lower panel images show hemoglobinized colonies. Wright-Giemsa stain of a cytospin of cells obtained from the CFU assay colonies (magnification ×60) is shown in the bottom row. The graph on the right panel shows quantification of the CFU assay (n=3). B. Immunophenotypic analysis of cells grown in the CFU assay. Right-hand graph shows quantification of surface marker expression in the cells from the CFU assay (n=3). hDMECs differentiated into several lineages, including erythroid CD235+, macrophage CD11b+, monocyte CD14+, myeloid CD33+ endothelial CD144+, and dendritic CD83+ cell progeny. C. Two week old neonatal immunodeficient NSG mice were sub-lethally irradiated (100 Rads) and transplanted with hDMEC-derived rEC-HMLPs ($5 \times 10^4$ cells). Analysis of peripheral blood of mice at 4, 6, and 12 weeks post-primary transplantation revealed circulating human CD45+ as well as their myeloid and erythroid progeny (n=6). D. Analysis of spleen of mice at 14 weeks post-primary transplantation revealed presence of human CD45+ as well as their lymphoid (CD19+ and CD56+) and myeloid (CD11b+ and CD41a+) progenies (n=3). Far right graph: first column, hCD45+ (%) measured against left hand y-axis; next four columns, $\log_2$ (% of hCD45+) measured against right hand y-axis. E. Analysis of bone marrow of mice at 14 weeks post-primary transplantation revealed presence of human CD45+ cells with small populations of both CD45+Lin−CD45RA−CD38−CD90+CD34+ and/or CD45+Lin−CD45RA−CD38−CD90−CD34+ cells that satisfy phenotypic definition of human HSCs and multi-potent progenitors (MPP), respectively (n=3). F. After 12 weeks the whole bone marrow of the mice transplanted with hDMEC-derived rEC-HMLPs were secondarily transplanted into adult (6-8 weeks old) NSG mice. Analysis of the peripheral blood of mice at 3 and 5 weeks post-secondary transplantation revealed circulating human CD45+ as well as their myeloid progeny (n=6). Far right graph: first two columns, hCD45+ (%) measured against left hand y-axis; last column, hCD33+ (%) measured against right y-axis.
Figure 4B:
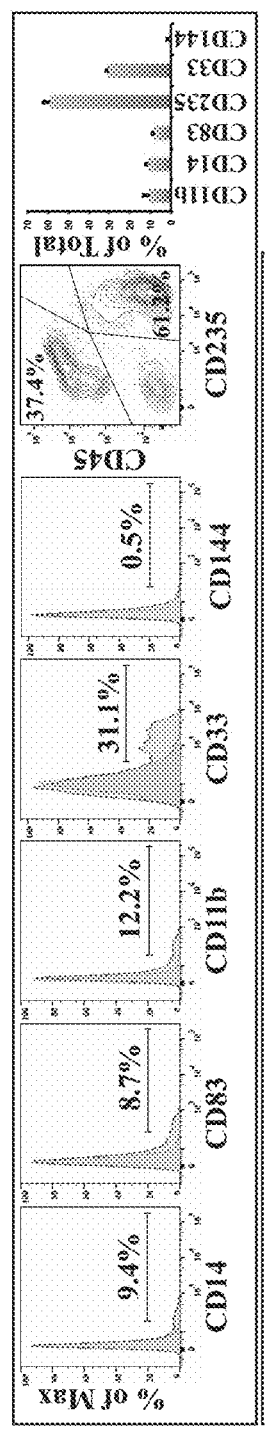

To test whether our method is applicable for reprogramming of ECs other than HUVECs, we used human adult dermal micro-vascular endothelial cells (hDMEC). Reprogramming of hDMECs into transplantable rEC-HMLPs is more relevant for potential future clinical applications because it might allow generation of transplantable autologous hematopoietic progenitors for bone-marrow reconstitution. In addition, as adult ECs may contain diminishingly low number of hemogenic ECs, this approach shows that a mature EC, but not a hemogenic or hemangioblastic EC, is being reprogrammed to hematopoietic cells.

hDMECs were transduced with the FGRS factors and underwent vascular induction in the serum-free environment (the same protocol used for the HUVEC reprogramming). To assess the in vitro functionality of the reprogrammed hDMECs we carried out a CFU assay. Four weeks after transduction of hDMECs with FGRS, GFP$^+$CD45$^+$CD34$^+$ cells were sorted and seeded at the density of 1200-1600 cells/cm$^2$ for CFU assays (n=3). Within 12-14 days the cells gave rise to cell aggregations morphologically resembling CFU-GM, CFU-GEMM, partially hemoglobinized BFU-E, and mixed colonies (FIG. 4A). Lineage specification in the CFU assay was verified by staining the colonies with Wright-Giemsa. We were able to detect cells with typical erythroid, macrophage, granulocyte, and megakaryocyte precursor morphologies (FIG. 4A). Immunophenotypic analysis of the colonies obtained from methylcellulose cultures revealed ability of the rEC-HMLPs derived from hDMECs to differentiate into several lineages, including erythroid CD235$^+$ (58.66±3.47%), macrophage CD11b$^+$ (10.39±3.05%), monocyte CD14$^+$ (10.87±1.28), and dendritic CD83$^+$ (7.94±0.80%) cell progeny (FIG. 4B).

HUVECs Cannot Spontaneously Generate rEC-HMLP-Like Cells.

To exclude the possibility that HUVECs could contain hemogenic or hemangioblastic cells that can spontaneously generate rEC-HMLP-like cells, we performed two sets of experiments.

First, we generated clonal cultures by sorting phenotypically marked mature HUVECs at densities of single-cell, two-cell, five-cell and 10-cells per well. To achieve this, we performed multi-color flow cytometry and sorted CD144 NE-cadherin)$^+$CD31$^+$E-selectin$^+$CD45$^-$ HUVECs in the configuration of 1, 2, 5, and 10 cells into 96-well plates. E-selectin (CD62E) is only expressed on the mature ECs and is absent on any hematopoietic or non-vascular cells. These colonies were then expanded into >10000 cell cultures (for 5 and 10-cell clones), >5000 cells (1-cell clone #1 and 2-cell clones), and >3000 cells (1-cell clone #2). Transduction of single-cell cultures, two-cell, five-cell, and ten-cell cultures with FGRS followed by co-culture with E4-HUVECs resulted in emergence of hematopoietic-like colonies similar to the colonies observed in a mixed HUVEC culture experiments. Because E-selectin is only expressed on mature terminally differentiated activated ECs, it is unlikely that contaminating "hemogenic or hemangioblastic" ECs were present in the clonal populations of FGRS transduced HUVECs and may have given rise to hematopoietic cells.

In the second set of experiments, we grew HUVECs in serum-free media that was used for reprogramming experiments. We compared proliferation as well as CD45, and CD34 expression in HUVECs in response to serum removal and combinatorial addition of hematopoietic cytokines in the culture media. Neither serum withdrawal, nor addition of optimal cocktails of hematopoietic cytokines caused any detectable expression of CD45 in HUVECs. However, both serum withdrawals alone and/or combined with TGFβ signaling inhibition caused significant up-regulation of CD34 expression in the HUVECs sustaining their vascular identity. Collectively, these data indicate that it is unlikely that FGRS reprograms pre-existing hemogenic or hemangioblastic precursor cells within the HUVECs, but rather that the FGRS TFs+ vascular induction protocol drives the conversion of terminally differentiated CD144$^+$CD31$^+$E-selectin$^+$CD45$^-$ ECs into hematopoietic cells.

rEC-HMLPs can Generate Phenotypically Correct HSPCs and Multi-Potent Progenitor Cells.

More detailed phenotypic analysis of rEC-HMLPs revealed small populations of cells that were CD45$^+$Lin$^-$CD45RA$^-$CD38$^-$CD90$^+$CD34$^+$ or CD45$^+$Lin$^-$CD45RA$^-$CD38$^-$CD90$^-$CD34$^+$, thus satisfying the criteria for phenotypically marked HSPCs or multi-potent progenitors, respectively, as defined by Chao, M. P. et al., (*Cold Spring Harb Symp Quant Biol*) 73:439-449 (2008) (FIG. 2B, n=3).

CD45$^+$ Cells have Potential for Expansion.

We compared expansion potential of CD45$^+$ and CD45$^-$ cells in serum-free hematopoietic medium. CD45$^+$ (12×10$^3$) and CD45$^-$ (60×10$^3$) cells were sorted into separate wells and expanded for two days. We observed 5-fold expansion of CD45$^+$ cells (56.6×10$^3$±7.9×10$^3$; n=3) and dramatic reduction of CD45$^-$ cells (4.6×10$^3$±1.0×10$^3$; n=3). To examine the potential of CD45$^+$ and CD45$^-$ cells for clonal expansion, they were sorted into 96-well plates at a density of 1 or 2 cells/well. After seven days of culture we observed CD45$^+$ cell expansion in 6.3±2.1 wells (93.1±14.5 cells/well) of 1-cell sort and 29.0±4.3 wells (112.1±21.2 cells/well) of the 2-cell sort (n=3). The difference between cell number/well in 1 and 2-cell sort was statistically not significant (p=0.78) suggesting that the difference in the number of wells with detected cell expansion was due to survival of sorted cells rather than a reflection of the number of cells sorted into a well. We did not detect any significant expansion of CD45⁻ cells.

Differentiation and Attempted Reprogramming of Human Embryonic Stem Cells.

We used a transgenic hESC reporter line that specifically identifies differentiated EC derivatives via a fluorescent reporter driven by a fragment of the human VE-cadherin promoter, as described in Rafii, S. et al., *Blood* 121:770-780 (2013). To augment endothelial commitment, hESC differentiation was initiated in co-culture with vascular feeder cells. Briefly, HUVEC were isolated and transduced with lentiviral AdE4ORF1 as described in Seandel, M. et al., *Proc Natl Acad Sci USA* 105:19288-19293 (2008). One day before plating hESCs to begin differentiation, MEF conditioned medium was replaced with hESC culture medium without FGF-2 and supplemented with 2 ng/ml BMP4. The next day, hESCs were plated directly onto an 80% confluent layer of E4ORF1⁺ ECs in hESC culture medium (without FGF-2, plus 2 ng/ml BMP4) and left undisturbed for 48 hours. This point of culture was considered as differentiation day zero. Cells were sequentially stimulated with recombinant cytokines in the following order: day 0 to 7—supplemented with 10 ng/ml BMP4; day 2 to 14—supplemented with 10 ng/ml VEGFA; day 2 to 14—supplemented with 5 ng/ml FGF-2; day 7 to 14—supplemented with 10 μM SB-431542. The fraction of hESC-derived cells co-expressing the vascular specific reporter and CD31 were harvested at day 14 by FACS. These cells were transduced with the FGRS cocktail and 2-3 days later plated on a layer of E4ORF1 HUVECs. The extent of reprogramming was assessed by flow cytometry.

Human Embryonic Stem Cells Lack Capability to Form Highly Proliferative HSCs.

Currently, differentiation of pluripotent stem cells, including embryonic stem cells (ESs) and induced pluripotent stem cells (iPSCs) into repopulating hematopoietic cells, shows limited success. Therefore, FGRS may be the missing factors that could augment differentiation of ECs derived from human ESs into HSCs. To this end, we differentiated hESs into ECs (hES-ECs)[38]. We then purified VEGFR2 positive hES-ECs and transduced them with FGRS. Notably, FGRS transduced hES-ECs could generate significant number of CD45⁺CD144⁻ cells. However, these CD45⁺CD144⁻ cells failed to form distinct stable hematopoietic-like colonies and did not enter a phase of highly proliferative growth. These results indicate that hES-ECs are not as permissive as HUVECs in being reprogrammed into rEC-HMPLs.

rEC-HMLPs Generated from ECs can be Transplanted and Function In Vivo to Replace Hematopoietic Cells.

To determine whether rEC-HMLPs were capable of in vivo engraftment, we transplanted 1.5×10⁶ of CD45⁺GFP⁺ rEC-HMLPs via retro-orbital injection into adult sub-lethally irradiated (275 Rad) immunocompromised NOD-SCID-IL2γ-receptor deficient (NSG) mice (n=9; one day post-radiation). Peripheral blood of the injected mice was tested at 2, 5, 12, 16 and 22 to 44 weeks post-transplantation for the presence of human CD45⁺ cells (FIG. 3B). We detected circulating human CD45⁺ cells at 2 (n=7; 17.38±7.73%), 5 (n=6; 15.1±13.39%), 12 (n=6; 14.14±5.44%), 16 (n=6; 22.36±17.95%) and 22 to 44 (n=6, 21.23±22.27%) weeks. Analysis of peripheral blood, bone marrow (BM), and spleen at 16 weeks post-transplantation revealed the presence of human CD45⁺ cells in all three tissues and human CD45⁻CD235⁺ erythroid cells in peripheral blood. BM and spleen were populated by myeloid progeny of rEC-HMLPs (CD45⁺CD33⁺) with a small but detectable number of CD41a⁺ (megakaryocyte) cells (FIG. 3C).

Transplanted rEC-HMLPs Retain their Ability to Generate Erythroid, Megakaryocyte, Macrophage, Monocyte, and Dendritic Cell Progeny.

To determine whether engrafted rEC-HMLP isolated from the host retained their multi-lineage potential, we carried out a secondary CFU assay. We isolated human CD45⁺ (hCD45⁺) from bone marrow of transplanted mice at 22 (n=1) and 24 (n=4) weeks post-transplantation. These cells were expanded in vitro for 24 hours and sorted for hCD45⁺ CD34⁺ cells for the CFU assay. Within 14 days plated cells gave rise to colonies with morphologies similar to CFU-GM, CFU-GEMM, and BFU-E. Wright-Giemsa stain of the cytospin of the cells revealed typical morphology of human myeloid progeny of the assayed cells. Immunophenotypic analysis of the methylcellulose culture revealed that the human CD45⁺ compartment contained CD41a⁺, CD14⁺, CD83⁺, and CD33⁺ cells, suggesting the presence of megakaryocyte, macrophage, monocyte, and dendritic cell progenies. The CD45⁻ compartment contained CD235⁺ and no mouse Teri 19⁺ cells, suggesting robust erythroid differentiation of human CD45⁺CD34⁺ cells in the CFU assay (FIG. 3E).

Figure 3A:
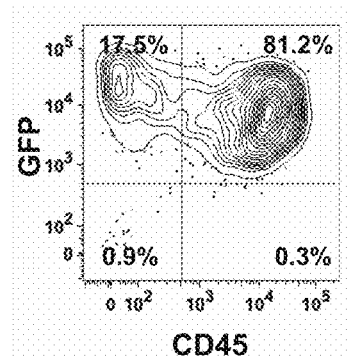
FIGS. 3A-3G. A. Reprogrammed cells ($1.5 \times 10^6$ of $CD45^+$ $GFP^+$ cells) were retro-orbitally injected into sub-lethally irradiated (275 Rad) mice (n=9; one day post-radiation). B. Circulating human $CD45^+$ cells were detected in the peripheral blood of the injected mice at 2, 5, 12, and 16 weeks. Circulating human $CD45^+$ cells were detected at 2 (n=7; 17.38±7.73%), 5 (n=6; 15.1±13.39%), 12 (n=6; 14.14±5.44%), and 22-40 (n=6; 21.23±22.27%) weeks. The 22-44 weeks (up to 10 months) engrafted mice were used for further analyses of the myelodysplasia and fibrotic changes. C. Analysis of the peripheral blood, bone marrow, and spleen at 16 weeks post-transplantation revealed presence of human CD45+ cells in all three tissues and hCD45−hCD235+ erythroid cells in peripheral blood. Results for BM are shown. BM and spleen were populated by myeloid progeny of rEC-HMLPs (CD45+CD33+) with a small but readily detectable number of CD41a+ (megakaryocyte) cells. D. FACS analysis of the methylcellulose culture revealed that CD45− compartment contained CD235+ (Glycophorin A) and no mouse Ter119+ cells suggesting robust erythroid differentiation of human CD45+CD34+ cells in the CFU assay. E. Phenotypic analysis of in vivo engrafted rEC-HMLPs in bone marrow showing small population of human cells that are phenotypically marked as CD45+Lin− CD45RA−CD38−CD90−CD34+ and satisfy the definition of multi-potent progenitors (MPPs). F. Identification of viral integration on a single-colony level. Lin−CD45RA−CD38−CD90−CD34+ cells were used for a CFU assay. Fourteen days after the start of the CFU assay 3 distinct cell aggregations/colonies were detected. Four PCR reactions were performed for each amplified colony using their genomic DNA as template. They revealed integration of all four FGRS viral vectors used for reprogramming (bottom image; Letters F-FOSB, G-GFI1, R-RUNX1, S-SPI1 show PCR products specific for each of these factors in the first colony.). G. Identification of viral integration on a single-cell level. Whole genome amplification (WGA) of 21 human CD45+ cells isolated from a host mouse 22 weeks after transplantation. The cells were sorted into a 96-well plate, with 1 cell per well, directly into a lysis buffer for the Phi29 based WGA. WGA was followed by a PCR reaction with primers specific to the CMV promoter and the transgene. Quantification of the analysis is shown. Nineteen cells showed integration of all four viruses (FGRS). Two cells showed integration of three viruses: FGS (RUNX1 was undetectable) and GRS (FOSB was undetectable).
Figure 3B:
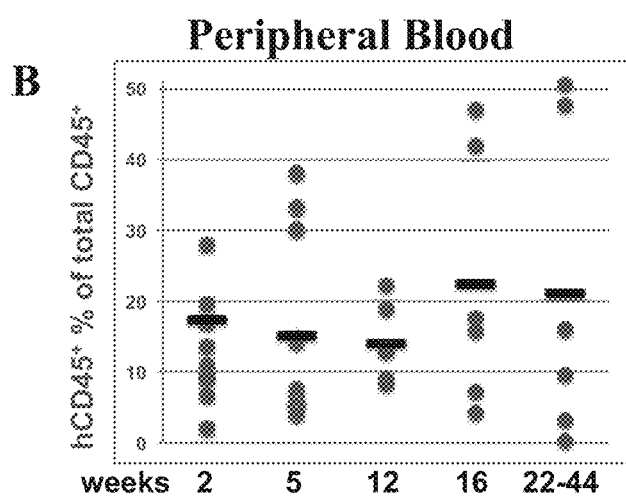
Figure 3C:
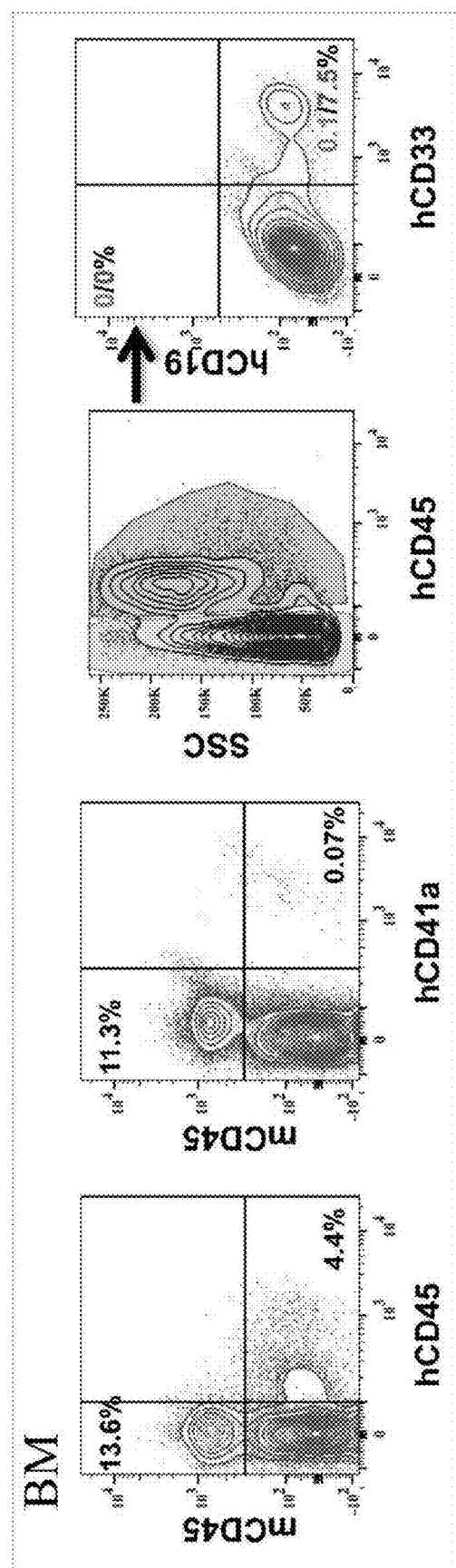
Figure 3D:
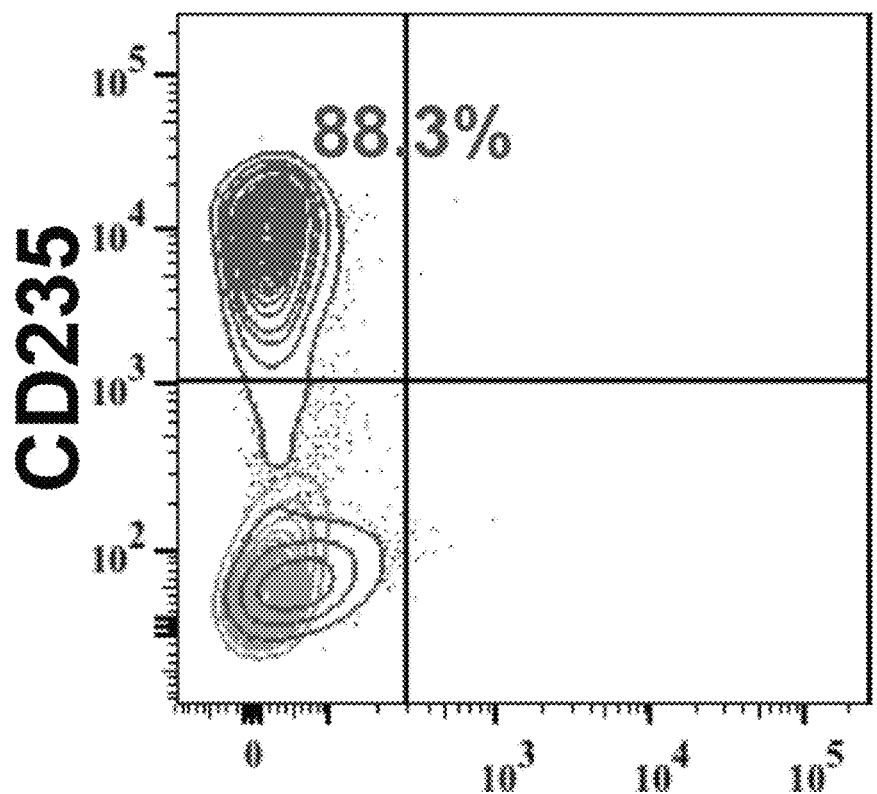
Figure 3E:
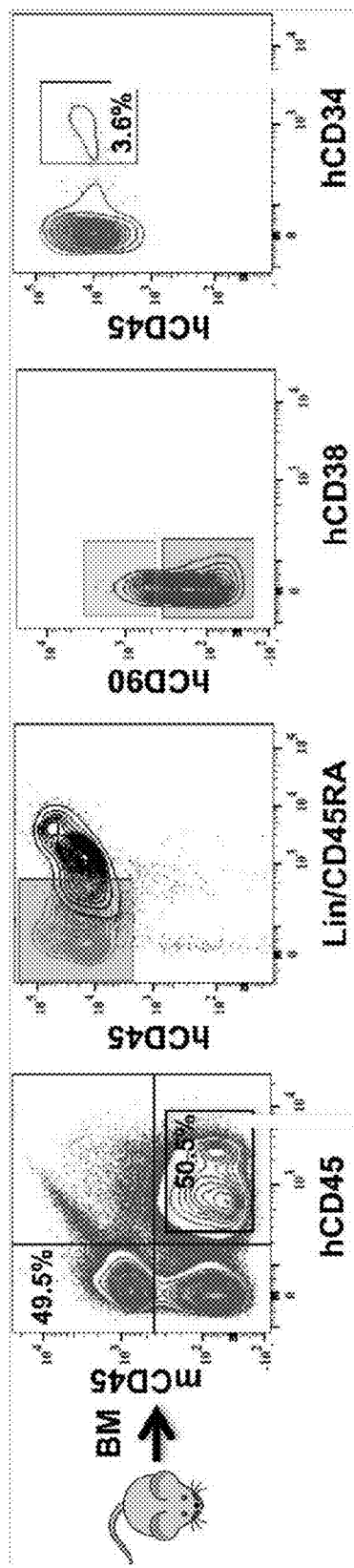
Figure 3F:
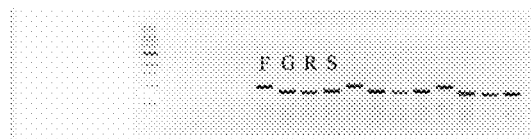
Figure 3G:
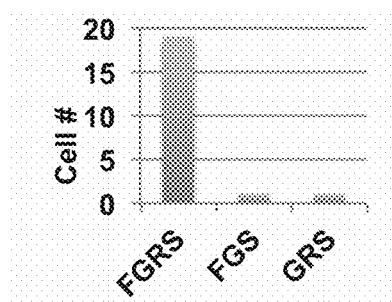

Analysis of the rEC-HMLPs engrafted in the bone marrow of the NSG mice revealed a small population of Lin⁻CD45RA⁻CD38⁻CD90⁻CD34⁺ cells that satisfy the definition of human multi-potent progenitors (FIG. 3E). To verify that these cells retain their multi-lineage potential and are derivatives of the reprogrammed rEC-HMLPs, we plated them for CFU assay and checked for viral integration in single colonies. Genomic DNA isolated from separate colonies was analyzed for the presence of four reprogramming factors. All tested colonies (n=3) were positive for lentiviral vectors expressing FOSB, GFI1, RUNX1, and SPI1 (FIG. 3F). To quantify the frequency of viral integration at single-cell level, we analyzed human CD45⁺ cells from the host bone marrow. Cells were sorted into a 96-well plate (1 cell/well) for whole genome amplification (WGA). Amplified genomic DNA was examined for viral integration. All cells (n=21) were positive for viral vector integration. Two cells showed integration of three (FGS with RUNX1 undetectable and GRS with FOSB undetectable) out of four viruses used for reprogramming (FIG. 3G). Results of the single-cell and single colony viral integration confirmed that human hematopoietic cells isolated from host mice originate from the engrafted rEC-HMLPs into the NSG mice.

Transplanted rEC-HMLPs Retain Genomic Integrity.

To assess the genomic integrity of CD45⁺ rEC-HMLPs (at day 35 post-transduction), and CD45⁺CD34⁺ rEC-HMLPs engrafted in the bone marrow of the NSG mice (24 weeks post-transplantation), we performed comparative genomic hybridization (CGH) analysis using Agilent SurePrint G3 Human CGH Microarray (1M probes). The analysis did not reveal genetic abnormalities, suggesting that proliferating rEC-HLMPs remain genetically stable both in vitro and in vivo.

Transplanted rEC-HMLPs do not Lead to Malignant Transformation In Vivo.

To address the concern of a possible malignant transformation of the transplanted rEC-HMLPs, including predisposition to myelodysplastic syndrome (MDS), we analyzed bone marrow, spleen, and liver of recipient mice for up to 10 months after transplantation (FIG. 3A). Peripheral blood was first analyzed for the presence of circulating hCD45+ cells. Mice showing engraftment were sacrificed and their spleen, liver, and tibia were analyzed for signs of the MDS. None of the mice manifested any gross evidence of leukemias and lymphomas, such as lymphadenopathy, splenomegaly or organomegaly. We also performed comprehensive analyses by employing a panel of staining on the bone marrow, spleen, and liver of the rEC-HMLPs engrafted mice. We did not observe any indication of excess deposition of collagen or desmin. Also, the microscopic architecture of the bone marrow manifests no evidence of fibrotic remodeling reminiscent of myelodysplastic syndrome. The osteoblastic, vascular and perivascular regions were morphologically intact. We conclude that our approach does not lead to induction of hematopoietic cells with leukomogenic potential.

Transplanted rEC-HMLPs Generate Lymphoid Cells.

Figure 6A:
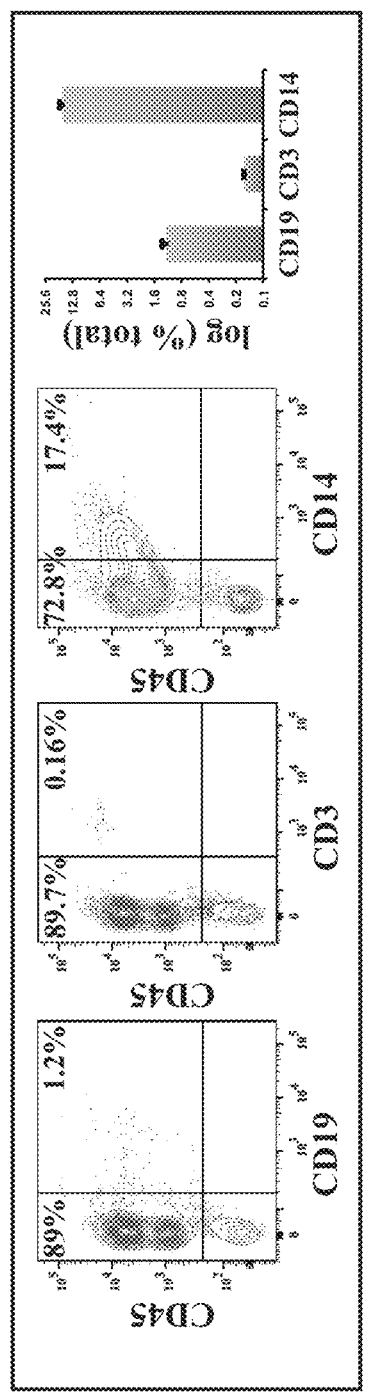
FIGS. 6A-6B. A. rEC-HMLPs differentiate into CD3+, CD19+ and CD14+ hematopoietic cells in the absence of exogenous expression of SPI1. The reprogrammed cells were transferred on a layer of bone marrow stromal cells (OP9) expressing Delta-like 4 (OP9-DL4) and grown in the presence of serum-free hematopoietic media (see Methods) supplemented with IL-7 (10 ng/ml), IL-11 (10 ng/ml), and IL-2 (5 ng/ml) and absence of doxycycline. B. Macrophages differentiated from rEC-HMLPs are capable of phagocytosis. The images show groups of firmly plastic-adherent CD11b+GFP+ cells with clearly visible ingested beads. Columns of images left to right: CFP fluorescence; nuclei of the cells stained with DAPI, fluorescent beads; CD11b staining; combined image of four panels on the left. Scale bar is 15 µm.

The number of the lymphoid progeny of the transplanted rEC-HMLPs derived from HUVECs (in spleen, bone marrow, and peripheral blood) was negligibly small suggesting that transplanted rEC-HMLPs did not sufficiently contribute to T-cell chimerism in vivo. To address the possibility that constitutive residual expression of SPI1 prevents rEC-HMLPs from differentiating into T-cells, we used a combination of constitutively expressed FGR factors and inducible SPI1 (SPI1-Tet-On). HUVECs were transduced with FGR+SPI1-Tet-On lentiviruses and grown on a layer of HUVEC feeder monolayers for 27 days in the presence of doxycycline. We observed formation of hematopoietic-like colonies and an increase of the number of CD45+ cells. HUVEC feeders were resistant to doxycycline and maintained their vascular niche function throughout the induction of the nascent hematopoietic cells. Next, the reprogrammed cells were transferred on a layer of bone marrow stromal cells (OP9) expressing Delta-like 4 (OP9-DL4) and grown in the presence of serum-free hematopoietic media supplemented with IL-7 (10 ng/ml), IL-11 (10 ng/ml), and IL-2 (5 ng/ml). The cells were tested for the expression of CD3, CD19, and CD14 (3 weeks of OP9-DL4 co-culture; FIG. 6A). Notably, we were able to reliably detect a small fraction of CD3+ cells (0.16±0.01%; n=3), a larger number of CD19+ (1.17±0.13%; n=3) and a very significant population of cells expressing CD14 (16.46±1.02%; n=3), indicating generation of T-cells.

Transplanted rEC-HMLPs Generate Functional Macrophages.

Figure 6B:
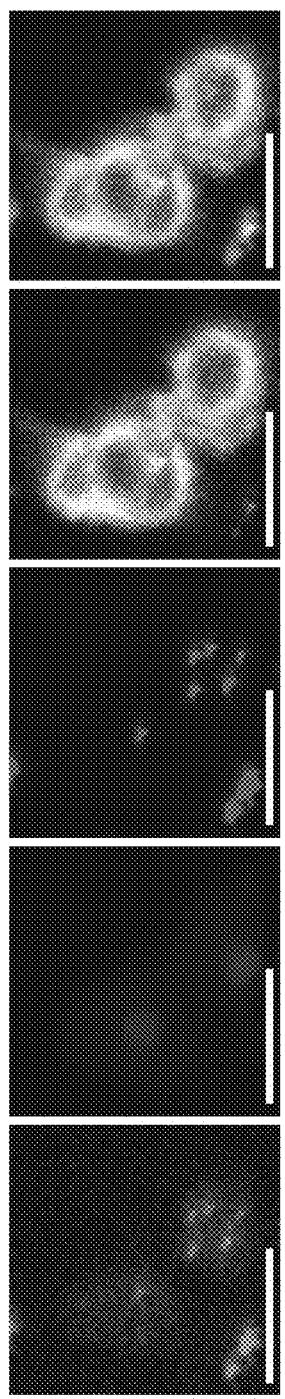

To conduct functional assessment of macrophages differentiated from rEC-HMLPs, we conducted a phagocytosis assay. rEC-HMLPs were cultured in the presence of M-CSF (10 ng/ml), SCF (10 ng/ml), (10 ng/ml), TPO (10 ng/ml), and 10% FBS for two weeks without a E4-HUVEC feeder layer. We observed an increase in size and granularity of the cultured cells. The culture was washed with PBS twice to remove non-adherent cells. Growth media mixed with red fluorescent beads at a low concentration of 1 µl/ml was applied to the attached cells for one hour at 37° C. After the incubation the cells were washed twice with PBS and live cells were stained with CD11b antibody. Cells were fixed and stained with DAPI for nuclear visualization. Confocal microscopy revealed groups of firmly attached CD11b+ GFP+ cells with clearly visible ingested beads (FIG. 6B). Thus, rEC-HMLPs can give rise to functional macrophages.

rEC-HMLPs Generated from hDMECs can be Transplanted and Function In Vivo to Replace Hematopoietic Cells.

Figure 4C:
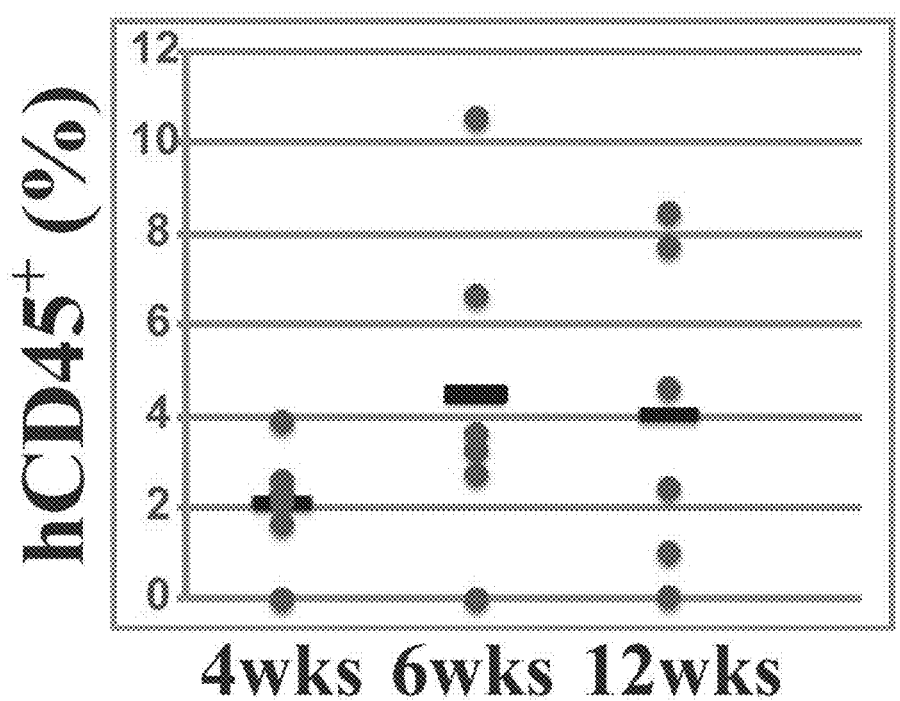
Figure 4D:
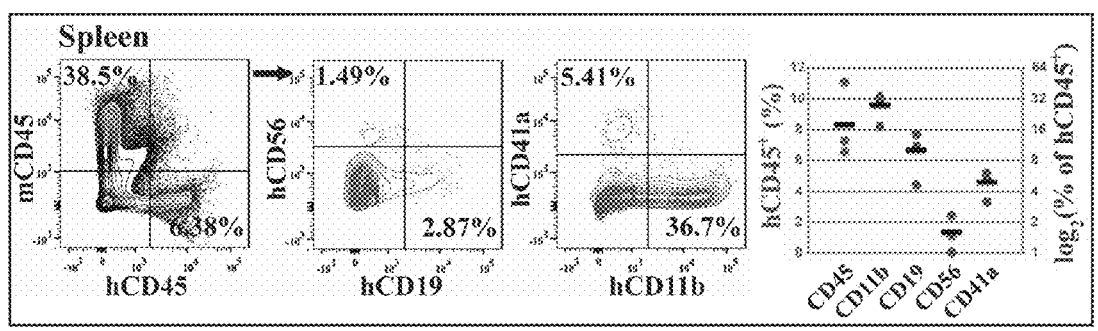

To determine whether rEC-HMLPs generated from hDMECs were capable of in vivo engraftment we transplanted 1×10$^5$ of CD45+GFP+ rEC-HMLPs via retro-orbital injection into sub-lethally irradiated (100 Rads) two weeks old neonatal NSG mice. Peripheral blood of the injected mice was tested at 4, 6, and 12 weeks post-transplantation for the presence of human CD45+ cells (FIG. 4C). We detected circulating human CD45+ cells at 4 (2.09±1.27%, n=6), 6 (4.46±3.66%, n=6), and 12 (4.05±3.50%, n=6) weeks. Analysis of peripheral blood, bone marrow, and spleen at 14 weeks post-transplantation revealed the presence of human CD45+ cells in all three tissues and human CD45−CD235+ erythroid cells in peripheral blood (FIG. 4C, D, E). Analysis of spleen at 14 weeks post-transplantation revealed small but distinct populations of CD19+ (10.13±4.98%; B-cells) and CD56+ (1.62±0.67%; NK-cells) cells of lymphoid progeny. These were in addition to CD11b+ (27.66±8.92%; macrophage) and CD41a+ (4.90±1.51%; megakaryocytes) myeloid cells (FIG. 4D).

Transplanted hDMEC-Derived rEC-HMLPs Also Retain Ability to Generate Functional HSC-Like Cells In Vivo.

Figure 4E:
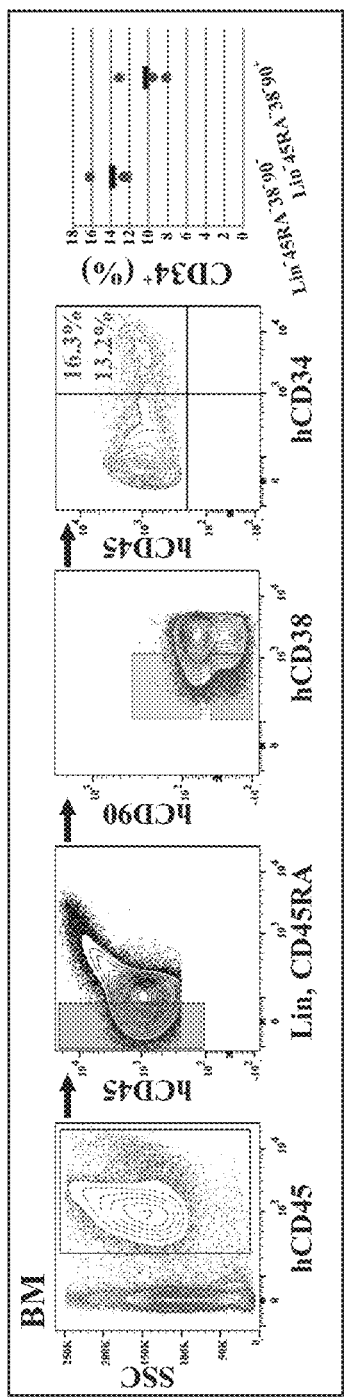
Figure 4F:
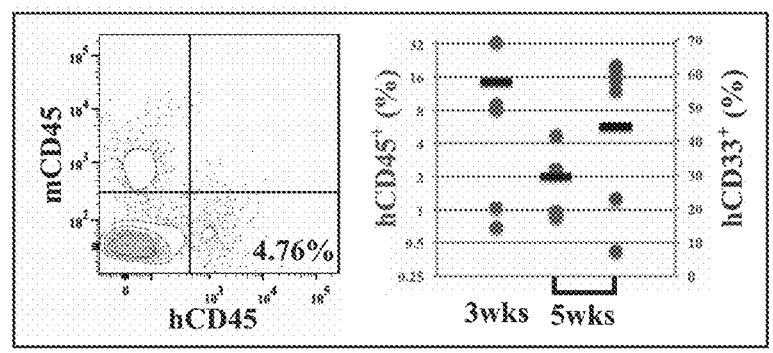

To functionally test whether transplanted hDMEC-derived rEC-HMLPs generated functional HSC-like cells in vivo we conducted secondary transplantations. We transplanted entire bone marrow from femurs of primary engrafted mice 12 weeks post-transplantation (n=10). Phenotypic analysis of the rEC-HMLPs engrafted in the bone marrow of donor mice at 14 weeks post-primary transplantation, revealed significant populations of both CD45+Lin−CD45RA−CD38−CD90+CD34+ (10.37±2.55%) and CD45+Lin−CD45RA−CD38−CD90−CD34+ (13.83±2.14%) cells that satisfy the phenotypic definition of human HSPCs and multi-potent progenitors (MPP), respectively (FIG. 4E). We detected hCD45+ in PB (peripheral blood) of the secondary recipients three (n=6; 14.61±15.7%) and five (n=6; 2.01±1.5%) weeks post-transplantation with a significant population of myeloid progeny (n=6; 44.32±23.21%) (FIG. 4F). Long-term primary engraftment and successful secondary short-term engraftment supports the existence of HSPC-like cells/self-renewing MPPs in the population of the reprogrammed hDMECs.

rEC-HMLPs Show Up-Regulation of Hematopoietic Genes and Downregulation of Vascular Genes.

Figure 5A:
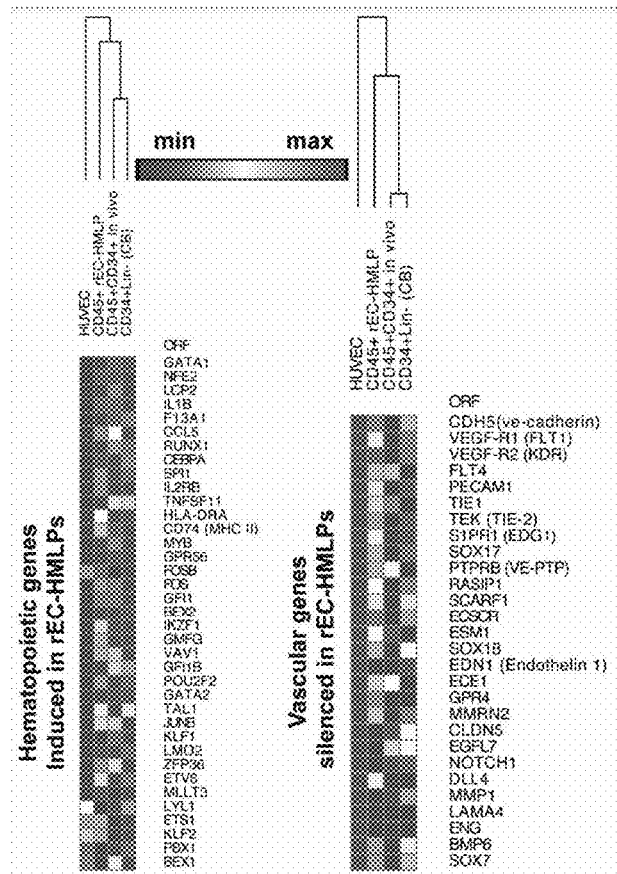
FIGS. 5A-5C. A. Global gene transcription profiling uncovers the hematopoietic genes that are turned on and vascular genes are that silenced in CD45+ rEC-HLMPs as well as in in vivo engrafted CD45+CD34+ rEC-HMLPs after 22 weeks post-transplantation. Both populations are compared to gene expression of HUVEC and CD34+Lin− umbilical cord blood cells. The data are presented as $\log_2$ (transcription level). B. Comparison of expression of prototypical pluripotency genes in HUVECs, CD45+ rEC-HLMPs, CD45+CD34+ rEC-HMLPs after 22 weeks post-transplantation, and CD34+Lin− cells with human embryonic stem cells (hESCs). Prototypical pluripotency genes, such as Oct4, Nanog, Sox2, and Myc were not up-regulated in the reprogrammed cells compared to hESCs and nave HUVECs, which indicates that the reprogramming of HUVECs into rEC-HMPLs was achieved without transitioning through a pluripotent state. C. Gene ontology (GO) analysis of the sites bound by SPI1 together with GFI1, and SPI1 separately. Each graph shows GO gene groups that may be implicated in the change of cellular identity from ECs to rEC-HMLPs. Consensus DNA binding motifs (p<0.01) for reprogramming factors and possible candidates are shown underneath each group graph. All values of up-regulated or down-regulated genes are |$\log_2$ (rEC-HMLP/HUVEC)|≥2.
Figure 5B:
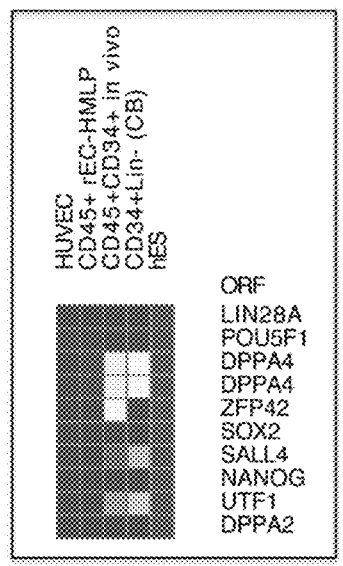

Next, we compared whole-genome transcription profiles of rEC-HMLPs to the gene expression profiles of cultured HUVECs and freshly isolated CD34+CD45Lin− cord blood hematopoietic cells to evaluate the extent of the reprogramming at the whole-genome transcriptome level (FIG. 5A). The analysis revealed up-regulation of hematopoietic genes and silencing of vascular gene expression in CD45 cells before transplantation and CD45+CD34+ rEC-HMLPs, 22 weeks post-transplantation, when compared to nave HUVECs and Lin−CD34+ CB cells. Prototypical pluripotency genes, such as Oct4, Nanog, Sox2, and Myc were not up-regulated in the reprogrammed cells compared to human embryonic stem cells (hESC) and nave HUVECs, which indicates that the reprogramming of HUVECs into rEC-HMPLs was achieved without transitioning through a pluripotent state (FIG. 5B). Hierarchical clustering of HUVECs, CD45+ rEC-HMLPs, CD45+CD34+ rEC-HMLPs whole-transcriptomes after 22 weeks post-transplantation, and CD34+Lin− cells with tighter clustering of CD45+CD34+ rEC-HMLPs and CB cells suggested additional in vivo "education/reprogramming" of rEC-HMLPs.

ChIP-Seq and Data Analysis.

ChIP-Seq was performed as described in Goldberg, A. D. et al., Cell 140:678-691 (2010). Briefly, cells were cross-linked for 15 min in 1.% paraformaldehyde, washed and lysed. Chromatin was sheared using Bioruptor to fragments of approximately 150 base pairs, washed and eluted. The eluted chromatin was reverse-cross-linked and column purified (SPI1 and GFI antibodies were obtained from Santa Cruz Biotechnology; catalogue numbers sc-352 and sc-8558.) ChIP samples were prepared for sequencing using Illumina TruSeq DNA Sample Preparation Kit according to the standard preparation protocol (Illumina). Sequencing service was performed on an Illumina Hiseq 2000 sequencer according to the standard Illumina protocol. ChIP-seq reads were aligned to the reference human genome (hg19, NCBI Build 37) using the BWA program (Li, H. et al., *Bioinformatics* 25:1754-1760 (2009)) and PCR duplicates were removed by Picard (available online from sourceforge). Unique reads mapped to a single best-matching location with no more than two mismatches were kept and used to generate genome-wide distribution of SPI1 and GFI1 binding and for peak identification. The software ChIPseeqer 2.0 (Giannopoulou, E. G. et al., *BMC Bioinformatics* 12:277 (2011)) was applied to the ChIP-Seq data with sequencing data from input DNA as control for identifying genomic enrichment of SPH and ChIP signals with FDR<0.005. Enrichment within +/-2 kb from transcription start site (TSS) was defined as promoter peaks. Selected genes were submitted for gene ontology (GO) analysis by DAVID (available online from the National Institute of Allergy and Infectious Diseases (NIAID), NIH) and motif analysis by HOMER (available online from biowhat, University of California, San Diego).

Identification of DNA Binding Sites of SPI1 and GFI1.

Figure 5C:
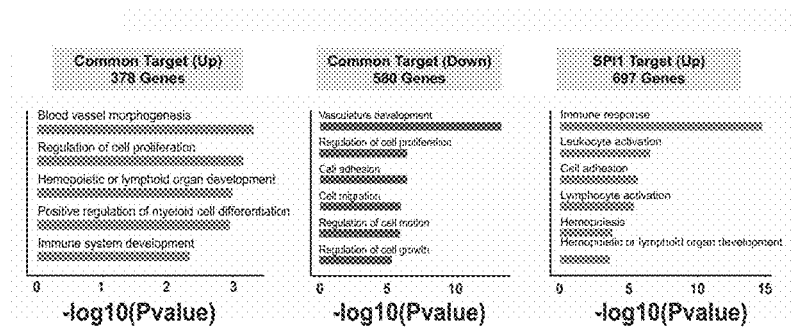

To elucidate possible mechanisms of the transcriptional FGRS mediated reprogramming of ECs into the rEC-HMLPs, we compared whole-genome DNA binding of the SPI1 and GFI1 in HUVECs using chromatin immune precipitation-coupled deep sequencing (ChIP-Seq). We identified 23587 SPI1-bound and 10999 GFI1-bound genomic sites in the +/-2 kb promoter region from transcription start sites (TSS). Notably, 91.6% of the GFI1-bound TSS (10079 of 10999) overlapped with SPI1-bound TSS. However, 57.3% SPI1-bound promoters were not occupied by GFI. Comparison of transcription levels of genes bound by SPI1, GFI1, or SPI1 and GFI1 together (Common Targets or "CT") revealed that most genes that are bound by GFI1 alone exhibit reduced levels of expression, whereas genes that are bound by either SPI1 alone or SPI1 in combination with GFI1 are up regulated. Gene ontology (GO) analysis of the bound sites uncovered a number of gene clusters that could be implicated in the change of cellular identity from ECs to rEC-HMLPs (FIG. 5C). GO revealed that up-regulated CTs ($\log_2$ (rEC-HMLP/HUVEC)≥2) belonged to clusters of genes with known functions in hematopoietic system development and myeloid differentiation, whereas a large number of down regulated CTs are known to be involved in vasculature development (FIG. 5C). Search for the known DNA binding motifs occupied by SPI1 and GFI1 TSS targets revealed that down regulated CTs (($\log_2$ (HUVEC/rEC-HMLP)≥2) contained a subset of genes with GFI1b (72 genes, p=0.001) and FOSB binding motifs (64 genes, p=0.0001). A subset of TSS of up regulated ($\log_2$ (rEC-HMLP/HUVEC)≥2) genes bound by SPI1 contained known DNA binding motifs of RUNX1 (133 genes, p=0.0001) and Fill (264 genes, p=0.01). In addition, a subset of CTs contained a known EBF (early B-cell factor) DNA binding motif (130 genes, p=0.01).

The whole-genome binding profile of SPI1 and GFI1 combined with the DNA binding motif search and whole-transcriptome expression analysis suggest that SPI1 alone and SPI1 in combination with GFI1 up regulate expression of hematopoietic genes. Notably, expression of vascular genes was suppressed by SPI1 and GFI1 as well as possibly FOSB. Up-regulation of hematopoietic genes depends on the expression of SPI1 that synergize with expression of RUNX1 and FLI1. Of note, FLI1 is equally expressed in nave HUVEC, CD45$^+$ rEC-HMLPs, CD45$^+$CD34$^+$ rEC-HMLPs 22 weeks post-transplantation, and Lin$^-$CD34$^+$ CB cells; normalized expression is 7.4, 7.9, 7.2, and 7.6, respectively.

To determine whether FGRS-induced reprogramming triggers endogenous expression of FGRS TFs, we determined the expression of the 5' and 3' un-translated regions (UTRs) by RNA-Seq. Because the lentiviral constructs used for reprogramming express open reading frames of the FGRS factors without UTRs, we were able to identify endogenously expressed transcripts by the presence of their UTR sequences. Analysis of 5' and 3' FGRS factors of the engrafted human rEC-HMLP using whole-transcriptome RNA-Seq revealed activation of endogenous expression of all four FGRS factors. Endogenous expression of FGRS TFs was calculated as a fraction of RNA-Seq reads that come from UTRs as Fraction (%)=UTR/(UTR+ORF), where UTR is the number of RNA-seq reads aligning to the 5' and 3' UTRs, ORF is the number of RNA-seq reads aligning to the open reading frame of the gene of interest. This analysis suggests that endogenous expression of the FGRS factors is activated in reprogrammed cells both in vitro (CD45$^+$ rEC-HMLPs) and after a period of in vivo microenvironmental-mediated education (CD45$^+$CD34$^+$ in vivo).

What is claimed is:

1. A method of generating human hematopoietic multi-lineage, progenitor cells (HMLPs) from human endothelial cells (ECs), comprising culturing human ECs expressing each of the transcription factors Finkel-Biskis-Dinkins murine osteosarcoma viral oncogene homolog B (FOSB), growth factor independent 1 transcription repressor (GFI1), Runt-related transcription factor 1 (RUNX1), spleen focus forming virus proviral integration oncogene (SPI1), in serum-free media with endothelial feeder cells, thereby generating HMLPs.

2. The method of claim 1, wherein said ECs are selected from fetal, neonatal, adult, or progenitor ECs.

3. The method of claim 2, wherein the ECs are selected from human umbilical vascular endothelial cells (HUVECs) or adult dermal micro-vascular endothelial cells (hDMECs).

4. The method of claim 1, wherein the endothelial feeder cells are human umbilical vascular endothelial cells (HUVECs) transformed to express either the adenovirus E4 open reading frame 1 (E4ORF1) gene, or the Akt gene.

5. The method of claim 1, wherein said Ed's are transduced with one or more vectors expressing FOSB, GFI1, RUNX1, and SPI1.

6. The method of claim 5, wherein at least one of said vectors further comprises a selectable marker.

7. The method of claim 6, wherein said selectable marker is an antibiotic resistance marker, an enzymatic marker, an epitope marker, or a visual marker.

8. The method of claim 6, wherein prior to culturing in the presence of the endothelial feeder cells, the ECs are enriched for expression of FOSB, GFI1, RUNX1, SPI1 or a combination thereof by selecting cells expressing at least one selectable marker.

9. The method of claim 5, wherein the expression of one or more of FOSB, GFI1, RUNX1, and SPI1 is inducible.

10. The method of claim 5, wherein the expression of one or more of FOSB, GFI1, RUNX1, and SPI1 is transient.

11. The method of claim 1, wherein said HMLPs can produce erythroid, lymphoid, myeloid, and megakaryocyte cells.

12. The method of claim 1, wherein the HMLPs are CD45+, and the method further comprising isolating HMLPs based on selection of CD45+ cells.

13. The method of claim 12, wherein the HLMPs are CD45+CD34+.

14. The method of claim 1, wherein the HMLPs comprise cells that are CD45+Lin−CD45RA−CD38−CD90+CD34+ or CD45+Lin−CD45RA−CD38−CD90−CD34+.

15. The method of claim 1, wherein said HMLPs can differentiate into hematopoietic cells after transplantation into a recipient.

16. The method of claim 1, wherein said ECs are cultured for at least five days to generate HMLPs.

17. The method of claim 1, wherein said ECs are grown in the presence of the endothelial feeder cells in a serum-free hematopoietic medium comprising bFGF, EGF, SCF, FLT3, TPO, and IL-6.

18. The method of claim 17, wherein said medium further comprises IGF-1, IGF-2, and IL-3.

19. The method of claim 17, wherein said medium is a hematopoietic stem cell medium.

* * * * *